United States Patent [19]

Adang

[11] Patent Number: 5,578,702
[45] Date of Patent: Nov. 26, 1996

[54] TOXIN ACTIVE AGAINST LEPIDOPTERAN INSECTS

[75] Inventor: Michael J. Adang, Athens, Ga.

[73] Assignee: Mycogen Plant Science, Inc., San Diego, Calif.

[21] Appl. No.: 150,506

[22] Filed: Nov. 10, 1993

Related U.S. Application Data

[63] Continuation of Ser. No. 713,624, Jun. 10, 1991, which is a continuation of Ser. No. 260,574, Oct. 20, 1988, abandoned, which is a continuation-in-part of Ser. No. 848,733, Apr. 4, 1986, abandoned, which is a continuation-in-part of Ser. No. 535,354, Sep. 26, 1983, abandoned.

[51] Int. Cl.$^6$ .......................... C12N 15/32; C07K 13/00
[52] U.S. Cl. ................ 530/350; 536/23.71; 435/69.1; 435/240.4; 800/205
[58] Field of Search ............... 536/23.71; 435/69.1, 435/70.1, 71.3, 240.4; 514/12; 530/350; 800/205

[56] References Cited

FOREIGN PATENT DOCUMENTS 0063949  11/1982  European Pat. Off. .

OTHER PUBLICATIONS

Held, G. A. et al. (1982) "Cloning and localization of the lepidopteran protoxin gene of *Bacillus thuringiensis* subsp. *kurstaki*" Proc. Natl. Acad. Sci. USA 79:6065–6069.

Klier, A. et al. (1982) "Cloning and expression of the crystal protein genes from *Bacillus thuringiensis* strain *berliner* 1715" EMBO J. 1:791–799.

Schnepf, H. E., H. R. Whiteley (1981) "Cloning and expression of the *Bacillus thuringiensis* crystal protein gene in *Escherichia coli*" Proc. Natl. Acad. Sci. USA 78:2893–2897.

Whiteley, H. R. et al. (1982) "Cloning the Crystal Protein Gene of *B. thuringiensis* in *E. coli*" in Molecular Cloning and Gene Regulation in Bacilli, pp. 131–144.

*Primary Examiner*—Che S. Chereskin
*Attorney, Agent, or Firm*—Saliwanchik & Saliwanchik

[57] ABSTRACT

A shortened or truncated protein toxin is provided which exhibits activity against lepidopteran insects. The truncated toxin is derived from an approximately 130 kD *Bacillus thuringiensis* delta-endotoxin. Also provided is a polynucleotide sequence encoding the truncated toxin.

1 Claim, 5 Drawing Sheets

TOXIN ACTIVE AGAINST LEPIDOPTERAN INSECTS

This application is a continuation of Ser. No. 07/713,624, filed Jun. 10, 1991, which is a continuation of Ser. No. 07/260,574, filed Oct. 20, 1988, now abandoned, which is a continuation-in-part of Ser. No. 06/848,733, filed Apr. 4, 1986, now abandoned, which is a continuation-in-part of Ser. No. 06/535,354, filed Sep. 26, 1983, now abandoned.

BACKGROUND

INSECTICIDAL PROTEIN

*Bacillus thuringiensis*, a species of bacteria closely related to *B. cereus*, forms a proteinacious crystalline inclusion during sporulation. This crystal is parasporal, forming within the cell at the end opposite from the developing spore. The crystal protein, often referred to as the δ-endotoxin, has two forms: a nontoxic protoxin of approximate molecular weight (MW) of 130 kilodaltons (kD), and a toxin having an approx. MW of 67 kD. The crystal contains the protoxin protein which is activated in the gut of larvae of a number of insect species. M. J. Klowden et al. (1983) Appl. Envir. Microbiol. 46:312–315, have shown solubilized protoxin from *B. thuringiensis* var. *israelensis* is toxic to *Aedes aegypti* adults. During activation, the protoxin is cleaved into two polypeptides, one or both of which are toxic. In vivo, the crystal is activated by being solubilized and converted to toxic form by the alkalinity and proteases of the gut. In vitro the protoxin may be solubilized by extremely high pH (e.g. pH 12), by reducing agents under moderately basic conditions (e.g. pH 10), or by strong denaturants (guanidium, urea) under neutral conditions (pH 7), and once solubilized, may be activated by the action of the protease trypsin. The crystal protein is reported to be antigenically related to proteins within both the spore coat and the vegetative cell wall. Carboyhdrate is not involved in the toxic properties of the protein.

*B. thuringiensis* and its crystalline endotoxin are useful because the crystal protein is an insecticidal protein known to be poisonous to the larvae of over a hundred of species of insects, most commonly those from the orders Lepidoptera and Diptera. Insects susceptible to the action of the *B. thuringiensis* crystal protein include, but need not be limited to, those listed in Table 1. Many of these insect species are economically important pests. Plants which can be protected by application of the crystal protein include, but need not be limited to, those listed in Table 2. Different varieties of *B. thuringiensis*, which include, but need not be limited to, those listed in Table 3, have different host ranges (R. M. Faust et al. (1982) in *Genetic Engineering in the Plant Sciences*, ed. N. J. Panapolous, pp. 225–254); this probably reflects the toxicity of a given crystal protein in a particular host. The crystal protein is highly specific to insects; in over two decades of commercial application of sporulated *B. thuringiensis* cells to crops and ornamentals there has been no known case of effects to plants or noninsect animals. The efficacy and safety of the endotoxin have been reviewed by R. M. Faust et al., supra. Other useful reviews include those by P. G. Fast (1981) in *Microbial Control of Pests and Plant Diseases*, 1970–1980, ed.: H. D. Burges, pp. 223–248, and H. E. Huber & P. Luthy (1981) in *Pathogenesis of Invertebrate Microbial Diseases*, ed.: E. W. Davidson, pp. 209–234.

The crystal protein gene usually can be found on one of several large plasmids that have been found in *Bacillus thuringiensis*, though in some strains it may be located on the chromosome (J. W. Kronstad et al. (1983) J. Bacteriol. 154:419–428). Several of the genes have been cloned into plasmids that can grow in *E. coli*. Whiteley's group (H. R. Whiteley et al. (1982) in *Molecular Cloning and Gene Regulation in Bactlli*, ed.: A. T. Ganesan et al., pp. 131–144, H. E. Schnepf & H. R. Whiteley (1981) Proc. Natl. Acad. Sci. U.S.A. 78:2893–2897, and European pat. application 63,949) reported the cloning of the toxin from *B. thuringiensis* var. *kurstaki* strains HD-1-Dipel and HD-73, using the enzymes Sau3AI (under partial digest conditions) and BglII, respectively, to insert large gene-bearing fragments having approximate sizes of 12 kbp and 16 kbp into the BamHI site of the *E. coli* plasmid vector pBR322. The HD-1 crystal protein was observed to be located on a 6.6 kilobase pair (kbp) HindIII fragment. Crystal protein from the HD-1-Dipel gene which was toxic to larvae, immunologically identifiable, and the same size as authentic protoxin, was observed to be produced by transformed *E. coli* cells containing pBR322 clones or subclones. This indicated that the Bacillus gene was transcribed, probably from its own promoter, and translated in *E. coli*. Additionally, this suggests that the toxic activity of the protein product is independent of the location of its synthesis. That the gene was expressed when the fragment containing it was inserted into the vector in either orientation suggests that transcription was controlled by its own promoter. The transcriptional and translational start sites, as well as the deduced sequence for the amino-terminal 333 amino acids of the HD-1-Dipel protoxin, have been determined by nucleic acid sequencing (H. C. Wong et al. (1983) J. Biol. Chem. 258:1960–1967). The insecticidal gene was found to have the expected bacterial ribosome binding and translational start (ATG) sites along with commonly found sequences at −10 and −35 (relative to the 5'-end of the mRNA) that are involved in initiation of transcription in bacteria such as *B. subtilis*. A. Klier et al. (1982) EMBO J. 1:791–799, have reported the cloning of the crystal protein gene from *B. thuringiensis* strain *berliner* 1715 in pBR322. Using the enzyme BamHI, a large 14 kbp fragment carrying the crystal protein gene was moved into the vector pHV33, which can replicate in both *E. coli* and Bacillus. In both *E. coli* and sporulating *B. subtilis*, the pHV33-based clone directed the synthesis of full-size (130 kD) protoxin which formed cytoplasmic inclusion bodies and reacted with antibodies prepared against authentic protoxin. Extracts of *E. coli* cells harboring the pBR322 or pHV33-based plasmids were toxic to larvae. In further work, A. Klier et al. (1983) Nucleic Acids Res. 11:3973–3987, have transcribed the berliner crystal protein gene in vitro and have reported on the sequence of the promoter region, together with the first 11 codons of the crystal protein. The bacterial ribosome binding and translational start sites were identified. Though the expected "−10" sequence was identified, no homology to other promoters has yet been seen near −35. Held et al. (1982) Proc. Natl. Acad. Sci. U.S.A. 77:6065–6069 reported the cloning of a crystal protein gene from the variety *kurstaki* in the phage λ-based cloning vector Charon4A. *E. coli* cells infected with one of the Charon clones produced antigen that was the same size as the protoxin (130 kD) and was toxic to larvae. A 4.6 kbp EcoRI fragment of this Charon clone was moved into pHV33 and an *E. coli* plasmid vector, pBR328. Again, 130 kD antigenically identifiable crystal protein was produced by both *E. coli* and *B. subtilis* strains harboring the appropriate plasmids. A *B. thuringiensis* chromosomal sequence which cross-hybridized with the cloned crystal protein gene was identified in *B. thuringiensis* strains which do not produce crystal protein during sporulation.

In addition to the crystal protein, *B. thuringiensis* produces at least three other toxins. Two of them, the α-exotoxin and γ-exotoxin, are phospholipases enzymes that degrade lipids. *B. cereus* is also known to produce phospholipases (or lecithinases) which are toxic to insect larve. Other bacterial enzymes which are involved in insect pathogenesis include, but need not be limited to, hyaluronidases, phosphatases, and proteases. Protease produced by *Pseudomonas aeruginosa* has been shown to have a specific affinity to proteins of *Galleria mellonella* larvae (see O. Lysenko & M. Kucera (1971) in Microbial Control of Insects and Mites, eds.: H. D. Burges & N. W. Hussey, pp. 205–227).

Shuttle Vectors

Shuttle vectors, developed by G. B. Ruvkun & F. M. Ausubel (1981) Nature 298:85–88, provide a way to insert foreign genetic materials into position of choice in a large plasmid, virus, or genome. There are two main problems encountered when dealing with large plasmids or genomes. Firstly, the large plamsids may have many sites for each restriction enzyme. Unique site-specific cleavage reactions are not reproducible and multi-site cleavage reactions followed by ligation lead to great difficulties due to the scrambling of the many fragments whose order and orientation one does not want changed. Secondly, the transformation efficiency with large DNA plasmids is very low. Shuttle vectors allow one to overcome these difficulties by facilitating the insertion, often in vitro, of the foreign genetic material into a smaller plasmid, then transferring, usually by in vivo techniques, to the larger plasmid.

A shuttle vector consists of a DNA molecule, usually a plasmid, capable of being introduced into the ultimate recipient bacteria. It also includes a copy of the fragment of the recipient genome into which the foreign genetic material is to be inserted and a DNA segment coding for a selectable trait, which is also inserted into the recipient genome fragment. The selectable trait ("marker") is conveniently inserted by transposon mutagenesis or by restriction enzymes and ligases.

The shuttle vector can be introduced into the ultimate recipient cell, typically a bacterium of the family Rhizobiaceae (which contains the genus Agrobacterium), by a tri-parental mating (Ruvkin & Ausubel, supra), direct transfer of a self-mobilizable vector in a bi-parental mating, direct uptake of exogenous DNA by Agrobacterium cells ("transformation", using the conditions of M. Holsters et al. (1978) Molec. Gen. Genet. 163:181–187), by spheroplast fusion of Agrobacterium with another bacterial cell, by uptake of liposome-encapsulated DNA, or infection with a shuttle vector that is based on a virus that is capable of being packaged in vitro. A tri-parental mating involves the mating of a strain containing a mobilizable plasmid, which carries genes for plasmid mobilization and conjugative transfer, with the strain containing the shuttle vector. If the shuttle vector is capable of being mobilized by the plasmid genes, the shuttle vector is transferred to the recipient cell containing the large genome, e.g. the Ti or Ri plasmids of Agrobacterium strains.

After the shuttle vector is introduced into the recipient cell, possible events include a double cross over with one recombinational event on either side of the marker. This event will result in transfer of a DNA segment containing the marker to the recipient genome replacing a homologous segment lacking the insert. To select for cells that have lost the original shuttle vector, the shuttle vector must be incapable of replicating in the ultimate host cell or be incompatible with an independently selectable plasmid pre-existing in the recipient cell. One common means of arranging this is to provide in the third parent another plasmid which is incompatible with the shuttle vector and which carries a different drug resistance marker. Therefore, when one selects for resistance to both drugs, the only surviving cells are those in which the marker on the shuttle vector has recombined with the recipient genome. If the shuttle vector carries an extra marker, one can then screen for and discard cells that contain plasmids resulting from a single cross-over event between the shuttle vector and the recipient plasmid resulting in cointegrates in which the entire shuttle vector is integrated with the recipient plasmid. If the foreign genetic material is inserted into or adjacent to the marker that is selected for, it will also be integrated into the recipient plasmid as a result of the same double recombination. It might also be carried along when inserted into the homologous fragment at a spot not within or adjacent to the marker, but the greater the distance separating the foreign genetic material from the marker, the more likely will be a recombinational event occurring between the foreign genetic material and marker, preventing transfer of the foreign genetic material.

If the shuttle vector is used to introduce a phenotypically dominant trait (e.g. a novel expressible insecticide structural gene, but not an inactivated oncogenic T-DNA gene) one need not rely on a double homologous recombination. The cells resulting from a single cross-over event resulting in cointegrate plasmids can transfer the desired trait into plant cells. One may even use a variant shuttle vector having a single uninterrupted sequence of T-DNA. However, as the resulting T-DNA will now contain a tandem duplication, one must be vigilant regarding a possible rare deletion of the shuttle vector by a single homologous recombination event occurring between the two homologous sequences in either the Agrobacterium or plant cells.

Shuttle vectors have proved useful in manipulation of Agrobacterium plasmids: see D. J. Garfinkel et al. (1981) Cell 27:143–153, A. J. M. Matzke & M.-D. Chilton (1981) J. Molec. Appl. Genet. 1:39–49, and J. Leemans et al. (1981) J. Molec. Appl. Genet. 1:149–164, who referred to shuttle vectors by the term "intermediate vectors".

A recently disclosed variation of the shuttle vector system for inserting changes into large DNA molecules is the "suicide vector". In this system, as described by A. Puhler et al., U.S. application Ser. No. 510,370 and R. Simon et al. (1983) in press, the shuttle vector is incapable of being maintained within the recipient cell. This property eliminates the need to introduce an incompatable plasmid into the recipient cell in order to exclude the shuttle vector as is commonly done during a triparental mating. All vectors which do not integrate into some already present DNA effectively "commit suicide" by not being replicated. As can be done with traditional types of shuttle vectors, one may distinguish between double and single homologous by screening for an antibiotic resistance gene which is not between the two regions of homology. Use of a pBR322-based suicide vector to transfer DNA sequences into a Ti plasmid has been reported by E. Van Haute et al. (1983) EMBO J. 2:411–417, and L. Comai et al. (1982) Plant. Molec. Biol. 1:291–300.

An alternative to the use of shuttle vectors for introduction of novel DNA sequences into T-DNA by means of homologous recombination involves bacterial transposons. As described in the section Agrobacterium-Genes on the TIP Plasmids, transposons can "jump" into the T-DNA of a TIP plasmid (e.g. see D. J. Garfinkel et al. (1981) Cell 27:143–153). Should the transposon be modified in vitro by the insertion of the novel sequence, that novel DNA can be transferred into the TIP plasmid's T-DNA by the transposon. The TIP can then transfer the novel DNA/transposon/T-DNA combination to a plant cell when it will be stably integrated.

Agrobacterium-Overview

Included within the gram-negative bacterial family Rhizobiaceae in the genus Agrobacterium are the species *A. tumefaciens* and *A. rhizogenes*. These species are respectively the causal agents of crown gall disease and hairy root disease of plants. Crown gall is characterized by the growth of a gall of dedifferentiated tissue. Hairy root is a teratoma characterized by inappropriate induction of roots in infected tissue. In both diseases, the inappropriately growing plant tissue usually produces one or more amino acid derivatives, known as opines, not normally produced by the plant which are catabolized by the infecting bacteria. Known opines have been classified into three main families whose type members are octopine, nopaline, and agropine. The cells of inappropriately growing tissues can be grown in culture, and, under appropriate conditions, be regenerated into whole plants that retain certain transformed phenotypes.

Virulent strains of Agrobacterium harbor large plasmids known as Ti (tumor-inducing) plasmids in *A. tumefaciens* and Ri (root-inducing) plasmids in *A. rhizogenes*. Curing a strain of these plasmids results in a loss of pathogenicity. The Ti plasmid contains a region, referred to as T-DNA (transferred-DNA), which in tumors is found to be integrated into the genome of the host plant. The T-DNA encodes several transcripts. Mutational studies have shown that some of these are involved in induction of tumorous growth. Mutants in the genes for tml, tmr, and tms, respectively result in large tumors (in tobacco), a propensity to generate roots, and a tendency for shoot induction. The T-DNA also encodes the gene for at least one opine synthase, and the Ti plasmids are often classified by the opine which they caused to be synthesized. Each of the T-DNA genes is under control of a T-DNA promoter. The T-DNA promoters resemble eukaryotic promoters in structure, and they appear to function only in the transformed plant cell. The Ti plasmid also carries genes outside the T-DNA region. These genes are involved in functions which include opine catabolism, oncogenicity, agrocin sensitivity, replication, and autotransfer to bacterial cells. The Ri plasmid is organized in a fashion analogous to the Ti plasmid. The set of genes and DNA sequences responsible for transforming the plant cell are hereinafter collectively referred to as the transformation-inducing principle (TIP). The designation TIP therefore includes both Ti and Ri plasmids. The integrated segment of a TIP is termed herein "T-DNA" (transferred DNA), whether derived from a Ti plasmid or an Ri plasmid.

M.-D. Chilton (June 1983) Sci. Amer. 248(6):50–59, has recently provided an introductory article on the use of Ti plasmids as vectors. Recent general reviews of Agrobacterium-caused disease include those by D. J. Merlo (1982) Adv. Plant Pathol. 1:139–178, L. W. Ream & M. P. Gordon (1982), Science 218:854–859, and M. W. Bevan & M.-D. Chilton (1982), Ann. Rev. Genet. 16:357–384; G. Kahl & J. Schell (1982) *Molecular Biology of Plant Tumors*, and K. A. Barton & M.-D. Chilton (1983) Meth. Enzymol. 101:527–539.

Agrobacterium-Infection of Plant Tissues

Plant cells can be transformed by Agrobacterium in a number of methods known in the art which include but are not limited to co-cultivation of plant cells in culture with Agrobacterium, direct infection of a plant, fusion of plant protoplasts with Agrobacterium spheroplasts, direct transformation by uptake of free DNA by plant cell protoplasts, transformation of protoplasts having partly regenerated cell walls with intact bacteria transformation of protoplasts by liposomes containing T-DNA, use of a virus to carry in the T-DNA, microinjection, and the like. Any method will suffice as long as the gene is reliably expressed, and is stably transmitted through mitosis and meiosis.

The infection of plant tissue by Agrobacterium is a simple technique well known to those skilled in the art (for an example, see D. N. Butcher et al. (1980) in *Tissue Culture Methods for Plant Pathologists*, eds.: D. S. Ingram & J. P. Helgeson, pp. 203–208). Typically a plant is wounded by any of a number of ways, which include cutting with a razor, puncturing with a needle, or rubbing with abrasive. The wound is then inoculated with a solution containing tumor-inducing bacteria. An alternative to the infection of intact plants is the inoculation of pieces of tissues such as potato tuber disks (D. K. Anand & G. T. Heberlein (1977) Amer. J. Bot. 64:153–158) or segments of tobacco stems (K. A. Barton, et al. (1983) Cell 32:1033–1043). After induction, the tumors cam be placed in tissue culture on media lacking phytohormones. Hormone independent growth is typical of transformed plant tissue and is in great contrast to the usual conditions of growth of such tissue in culture (A. C. Braun (1956) Cancer Res. 16:53–56).

Agrobacterium is also capable of infecting isolated cells and cells grown in culture (L. Mátron et al. (1979) Nature 277:129–131) and isolated tobacco mesophyll protoplasts. In the latter technique, after allowing time for partial regeneration of new cell walls, Agrobacterium cells were added to the culture for a time and then killed by the addition of antibiotics. Only those cells exposed to *A. tumefaciens* cells harboring the Ti plasmid were capable of forming calli when plated on media lacking hormone. Most calli were found to contain an enzymatic activity involved in opine anabolum. Other workers (R. B. Horsch & R. T. Fraley (18 Jan. 1983) 15th Miami Winter Symposium) have reported transformations by co-cultivation, leading to a high rate (greater than 10%) of calli displaying hormone-independent growth, with 95% of those calli making opines. M. R. Davey et al. (1980) in Ingram & Helgeson, supra, pp. 209–219, describe the infection of older cells that had been regenerated from protoplasts.

Plant protoplasts can be transformed by the direct uptake of TIP plasmids. M. R. Davey et al. (1980) Plant Sci. Lett. 18:307–313, and M. R. Davey et al. (1980) in Ingram & Helgeson, supra, were able to transform Petunia protoplasts with the Ti plasmid in the presence of poly-L-α-ornithine to a phenotype of opine synthesis and hormone-independent growth in culture. It was later shown (J. Draper et al. (1982) Plant and Cell Physiol. 23:451–458, M. R. Davey et al. (1982) in *Plant Tissue Culture* 1982, ed: A. Fujiwara, pp. 515–516) that polyethelene glycol-stimulated Ti plasmid uptake and that some T-DNA sequences were integrated into the genome. F. A. Krens et al. (1982) Nature 296:72–74, reported similar results using polyethelene glycol following by a calcium shock, though their data suggests that the integrated T-DNA included flanking Ti plamid sequences.

An alternative method to obtain DNA uptake involves the use of liposomes. The preparation of DNA containing liposomes is taught by Papahadjopoulos in U.S. Pat. Nos. 4,078,052 and 4,235,871. Preparations for the introduction of Ti-DNA via liposomes have been reported (T. Nagata et al. (1982) in Fujiwara, supra, pp. 509–510, and T. Nagata (1981) Mol. Gen. Genet. 184:161–165). An analogous system involves the fusion of plant and bacterial cells after removal of their cell walls. An example of this technique is the transformation of Vinca protoplast by Agrobacterium spheroplasts reported by S. Hasezawa et al. (1981) Mol. Gen. Genet. 182:206 210. Plant protoplasts can take up cell wall delimited Agrobacterium cells (S. Hasezawa et al. (1982) in Fujiwara, supra pp. 517–518).

T-DNA can be transmitted to tissue regenerated from a fusion of two protoplasts, only one of which had been transformed (G. J. Wullems et al. (1980) Theor. Appl. Genet. 56:203–208). As detailed in the section on Regeneration of Plants, T-DNA can pass through meiosis and be transmitted to progeny as a simple Mendelian trait.

Agrobacterium—Regeneration of Plants

Differentiated plant tissues with normal morphology have been obtained from crown gall tumors. A. C. Braun & H. N. Wood (1976) Proc. Natl. Acad. Sci. U.S.A. 73:496–500, grafted tobacco teratomas onto normal plants and were able to obtain normally appearing shoots which could flower. The shoots retained the ability to make opines and to grow independently of phytohormones when placed in culture. In the plants screened, these tumorous phenotypes were not observed to be transmitted to progeny, apparently being lost during meiosis (R. Turgeon et al. (1976) Proc. Natl. Acad. Sci. U.S.A. 73:3562–3564). Plants which had spontaneously lost tumorous properties, or which were derived from teratoma seed, were initially shown to have lost all their T-DNA (F.-M. Yang et al. (1980) In Vitro 16:87–92, F. Yang et al. (1980) Molec. Gen. Genet. 177:707–714, M. Lemmers et al. (1980) J. Mol. Biol. 144:353–376). However, later work with plants that had become revertants after hormone treatment (1 mg/l kinetin) showed that plants which had gone through meiosis, though loosing T-DNA genes responsible for the transformed phenotype, could retain sequences homologous to both ends of T-DNA (F. Yang & R. B. Simpson (1981) Proc. Natl. Acad. Sci. U.S.A. 78:4151–4155). G. J. Wullems et al. (1981) Cell 24:719–724, further demonstrated that genes involved in opine anabolism were capable of passing through meiosis though the plants were male sterile and that seemingly unaltered T-DNA could be inherited in a Mendelian fashion (G. Wullems et al. (1982) in Fujiwara, supra). L. Otten et al. (1981) Molec Gen. Genet. 183:209–213, used In7 transposon-generated Ti plasmid mutants in the tms (shoot-inducing) locus to create tumors which proliferated shoots. When these shoots were regenerated into plants, they were found to form self-fertile flowers. The resultant seeds germinated into plants which contained T-DNA and made opines. In further experiments, H. DeGreve et al. (1982) Nature 300:752–755, have found that octopine synthase can be inherited as a single dominant Mendelian gene. However, the T-DNA had sustained extensive deletions of functions other than ocs while undergoing regeneration from callus. Similar experiments with a tmr (root-inducing) mutant showed that full-length T-DNA could be transmitted through meiosis to progeny, that in those progeny nopaline genes could be expressed, though at variable levels, and that cotransformed yeast alcohol dehydrogenase I gene was not expressed (K. A. Barton et al. (1983) Cell 32:1033–1043). It now appears that regenerated tissues which lack T-DNA sequences are probably decended from untransformed cells which "contaminate" the tumor (G. Ooms et al. (1982) Cell 30:589–597). Recent work by A. N. Binns (1983) Planta 158:272–279, indicates that tumorogenic genes, in this case tmr, can be "shut off" during regeneration and "turned back on" by placing regenerated tissue in culture.

Roots resulting from transformation from *A. rhizogenes* have proven relatively easy to regenerate directly into plantlets (M.-D. Chilton et al. (1982) Nature 295:432–434.

Agrobacterium—Genes on the TIP Plasmids

A number of genes have been identified within the T-DNA of the TIP plasmids. About half a dozen octopine plasmid T-DNA transcripts have been mapped (S. B. Gelvin et al. (1982) Proc. Natl. Acad. Sci. U.S.A. 79:76–80, L. Willmitzer et al. (1982) EMBO J. 1:139–146) and some functions have been assigned (J. Leemans et al. (1982) EMBO J. 1:147–152). Some of these transcripts, specifically those in the region encoding tmr and tms, can also be transcribed in prokaryotic cells (G. Schröder et al. (1983) EMBO J. 2:403–409). The four genes of an octopine type plasmid that have been well defined by transposon mutagenesis include tms, tmr, and tml (D. J. Garfinkel et al. (1981) Cell 27:143–153). Ti plasmids which carry mutations in these genes respectively incite tumorous calli of *Nicotiana tabacum* which generate shoots, proliferate roots, and are larger than normal. In other hosts, mutants of these genes can induce different phenotypes (see M. W. Bevan & M.-D. Chilton (1982) Ann. Rev. Genet. 16:357–384). The phenotypes of tms and tmr are correlated with differences in the phytohormone levels present in the tumor. The differences in cytokinin:auxin ratios are similar to those which in culture induce shoot or root formation in untransformed callus tissue (D. E. Akiyoshi et al. (1983) Proc. Natl. Acad. Sci. U.S.A. 80:407–411). T-DNA containing a functional gene for either tms or tmr alone, but not functional tml alone, can promote significant tumor growth. Promotion of shoots and roots is respectively stimulated and inhibited by functional tml (L. W. Ream et al. (1983) Proc. Natl. Acad. Sci. U.S.A. 80:1660–1664). Mutations in T-DNA genes do not seem to affect the insertion of T-DNA into the plant genome (Leemans et al. (1982) supra, Ream et al. (1983) supra). The ocs gene encodes octopine synthase, which has been sequenced by H. De Greve et al. (1982) J. Mol. Appl. Genet. 1:499–511. It does not contain introns (intervening sequences commonly found in eukaryotic genes which are post-transcriptionally spliced out of the messenger precursor during maturation of the mRNA). It does have sequences that resemble a eukaryotic transcriptional signal ("TATA box") and a polyadenylation site. All of the signals necessary for expression of the ocs gene are found within 295 bp of the ocs transcriptional start site (C. Koncz et al. (1983) EMBO J. 2:1597–1603).

Nopaline Ti plasmids encode the nopaline synthase gene (nos), which has been sequenced by A. Depicker et al. (1982) J. Mol. Appl. Genet. 1:561–573. As was found with the ocs gene, nos is not interrupted by introns. It has two putative polyadenylation sites and a potential "TATA box". In contrast to ocs, nos is preceeded by a sequence which may be a transcriptional signal known as a "CAT box". All of the signals necessary for expression of the nos gene are found within 261 bp of the nos transcriptional start site (C. Koncz et al., supra). A gene for agrocinopine synthase and genes equivalent to tms and tmr have been identified on a nopaline-type plasmid (H. Joos et al. (1983) Cell 32:1057–1067), and a number of transcripts have been mapped (L. Willmitzer et al. (1983) Cell 32:1045–1056). J. C. McPhersson et al. (1980) Proc. Natl. Acad. Sci. U.S.A. 77:2666–2670, reported the in vitro translation of T-DNA encoded mRNAs from crown gall tissues.

Transcription from hairy root T-DNA has also been detected (L. Willmitzer et al. (1982) Mol. Gen. Genet. 186:16–22). Functionally, the hairy root syndrome appears to be equivalent of a crown gall tumor incited by a Ti plasmid mutated in tmr (F. F. White & E. W. Nester (1980.) J. Bacteriol. 144:710–720.

In eukaryotes, methylation (especially of cytosine residues) of DNA is correlated with transcriptional inactivation;

genes that are relatively under methylated are transcribed into mRNA. S. B. Gelvin et al. (1983) Nucleic Acids Res. 11:159–174, has found that the T-DNA in crown gall tumors is always present in at least one unmethylated copy. That the same genome may contain numerous other copies of T-DNA which are methylated suggests that the copies of T-DNA in excess of one may be biologically inert. (See also G. Ooms et al. (1982) Cell 30:589–597.)

The Ti plasmid encodes other genes which are outside of the T-DNA region and are necessary for the infection process. (See M. Holsters et al. (1980) Plasmid 3:212–230 for nopaline plasmids, and H. De Greve et al. (1981) Plasmid 6:235–248, D. J. Garfinkel and E. W. Nester (1980) J. Bacteriol 144:732–743, and G. Ooms (1980) J. Bacteriol 144:82–91 for octopine plasmids). Most important are the onc genes, which when mutated result in Ti plasmids incapable of oncogenicity. (These loci are also known as vir, for virulence.) Several onc genes have been accurately mapped and have been found to be located in regions conserved among various Ti plasmids (H. J. Klee et al. (1983) J. Bacteriol. 153:878–883, V. N. Iyer et al. (1982) Mol. Gen. Genet. 188:418–424). The onc genes function in trans, being capable of causing the transformation of plant cells with T-DNA of a different plasmid type and physically located on another plasmid (J. Hille et al. (1982) Plasmid 7:107 118, H. J. Klee et al. (1982) J. Bacteriol 150:327–331, A. J. de Framond et al. (1983) Biotechnol. 1:262–269). Nopaline Ti DNA has direct repeats of about 25 base pairs immediately adjacent to the left and right borders of the T-DNA which might be involved in either excision from the Ti plasmid or integration into the host genome (N. S. Yadav et al. (1982) Proc. Natl. Acad. Sci. U.S.A. 79:6322–6326), and a homologous sequence has been observed adjacent to an octopine T-DNA border (R. B. Simpson et al. (1982) Cell 29:1005–1014). Opine catabolism is specified by the occ and noc genes, respectively, of octopine- and nopaline-type plasmids. The Ti plasmid also encodes functions necessary for its own reproduction including an origin of replication. Ti plasmid transcripts have been detected in *A. tumefaciens* cells by S. B. Gelvin et al. (1981) Plasmid 6:17–29, who found that T-DNA regions were weakly transcribed along with non-T-DNA sequences. Ti plasmid-determined characteristics have been reviewed by Merlo, supra (see especially Table II), and Ream & Gordon supra.

Agrobacterium—TIP Plasmid DNA

Different octopine-type Ti plasmids are nearly 100% homologous to each other when examined by DNA hybridization (T. C. Currier & E. W. Nester (1976) J. Bacteriol. 126:157–165) or restriction enzyme analysis (D. Sciaky et al. (1978) Plasmid 1:238–253). Nopaline-type Ti plasmids have as little as 67% homology to each other (Currier & Nester, supra). A survey revealed that different Ri plasmids are very homologous to each other (P. Costantino et al. (1981) Plasmid 5:170–182). N. H. Drummond & M.-D. Chilton (1978) J. Bacteriol. 136:1178–1183, showed that proportionally small sections of octopine- and nopaline-type Ti plasmids were homologous to each other. These homologies were mapped in detail by G. Engler et al. (1981) J. Mol. Biol. 152:183–208. They found that three of the four homologous regions were subdivided into three (overlapping the T-DNA), four (containing some onc genes), and nine (having onc genes) homologous sequences. The uninterrupted homology contains at least one tra gene (for conjugal transfer of the Ti plasmid to other bacterial cells), and genes involved in replication and incompatibility. This uninterrupted region has homology with a Sym plasmid (involved in symbiotic nitrogen fixation) from a species of Rhizobium, a different genus in the family Rhizobiaceae (R. K. Prakash et al. (1982) Plasmid 7:271–280). The order of the four regions is not conserved, though they are all oriented in the same direction. Part of the T-DNA sequence is very highly conserved between nopaline and octopine plasmids (M.-D. Chilton et al. (1978) Nature 275:147–149, A. Depicker et al. (1978) Nature 275:150–153). Ri plasmids have been shown to have extensive homology among themselves, and to both octopine (F. F. White & E. W. Nester (1980) J. Bacteriol. 144:710–720) and nopaline (G. Risuleo et al. (1982) Plasmid 7:45–51) Ti plasmids, primarily in regions encoding onc genes. Ri T-DNA contains extensive though weak homologies to T-DNA from both types of Ti plasmid (L. Willmitzer et al. (1982) Mol. Gen. Genet. 186:16–22). Plant DNA from uninfected *Nicotiana glauca* contains sequences, referred to as cT-DNA (cellular T-DNA), that show homology to a portion of the Ri T-DNA (F. F. White et al. (1983) Nature 301:348–350, L. Spano et al. (1982) Plant Molec. Biol. 1:291–300). G. A. Huffman et al. (1983) J. Bacteriol., have mapped the region of cross-hybridization and have shown that Ri plasmid, pRiA4b, is more closely related to a pTiA6 (octopine-type) than pTiT37 (nopaline-type) and that this Ri plasmid appears to carry sequence homologous to tms but not tmr. Their results also suggested that Ri T-DNA may be discontinuous, analogous to the case with octopine T-DNA.

It has been shown that a portion of the Ti (M.-D. Chilton et al. (1977) Cell 11:263–271) or Ri (M.-D. Chilton (1982) Nature 295:432–434, F. F. White et al. (1982) Proc. Natl. Acad. Sci. U.S.A. 79:3193–3197, L. Willmitzer (1982) Mol. Gen. Genet. 186:16–22) plasmid is found in the DNA of tumorous plant cells. The transferred DNA is known as T-DNA. T-DNA is integrated into the host DNA (M. F. Thomashow et al. (1980) Proc. Natl. Acad. Sci. U.S.A. 77:6448 6452, N. S. Yadav et al. (1980) Nature 287:458–461) in the nucleus (M. P. Nuti et al. (1980) Plant Sci. Lett. 18:1–6, L. Willmitzer et al. (1980) Nature 287:359–361, M.-D. Chilton et al. (1980) Proc. Natl. Acad. Sci. U.S.A. 77:4060 4064).

M. F. Thomashow et al (1980) Proc. Natl. Acad. Sci. U.S.A. 77:6448–6452, and M. F. Thomashow et al, (1980) Cell 19:729–739, found the T-DNA from octopine-type Ti plasmids to have been integrated in two separate sections, TL-DNA and TR-DNA, left and right T-DNAs respectively. The copy numbers of TR and TL can vary (D. J. Merlo et al. (1980.) Molec. Gen. Genet. 177:637–643). A core of T-DNA is highly homologous to nopaline T-DNA (Chilton et al. (1978) supra, and Depicker et al. (1978) supra), is required for tumor maintenance, is found in TL, is generally present in one copy per cell, and codes for the genes tms, tmr, and tml. On the other hand TR can be totally dispensed with (M. De Beuckeleer et al. (1981) Molec. Gen. Genet. 183:283–288, G. Ooms et al. (1982) Cell 30:589–597), though found in a high copy number (Merlo et al. (1980) supra). G. Ooms et al. (1982) Plasmid 7:15–29, hypothesized that TR is involved in T-DNA integration, though they find that when TR is deleted from the Ti plasmid, *A. tumefaciens* does retain some virulence. G. Ooms et al. (1982) Cell 30:589–597, showed that though T-DNA is occasionally deleted after integration in the plant genome, it is generally stable and that tumors containing a mixture of cells that differ in T-DNA organization are the result of multiple transformation events. The ocs is found in TL but can be deleted from the plant genome without loss of phenotypes related to tumorous growth. The left border of integrated TL has been observed to be composed of repeats of T-DNA sequences which are in either direct or inverted orientations (R. B. Simpson et al. (1982) Cell 29:1005–1014).

In contrast to the situation in octopine-type tumors, nopaline T-DNA is integrated into the host genome in one continuous fragment (M. Lemmers et al. (1980) J. Mol. Biol. 144:353–376, P. Zambryski et al. (1980) Science 209:1385–1391). Direct tandem repeats were observed. T-DNA of plants regenerated from teratomas had minor modifications in the border fragments of the inserted DNA (Lemmers et al., supra). Sequence analysis of the junction between the right and left borders revealed a number of direct repeats and one inverted repeat. The latter spanned the junction (Zambryski et al. (1980) supra). The left junction has been shown to vary by at least 70 base pairs while the right junction varies no more than a single nucleotide (P. Zambryski et al. (1982) J. Molec. Appl. Genet. 1:361–370). Left and right borders in junctions of tandem arrays where separated by spacers which could be over 130 bp. The spacers were of unknown origin and contained some T-DNA sequences. T-DNA was found to be integrated into both repeated and low copy number host sequences. H. Joos et al. (1983) Cell 32:1057–1067, have shown that virulence is not eliminated after deletion of either of the usual nopaline T-DNA borders.

Simpson et al. (1982) supra, and Zambryski et al. (1980) supra have suggested that direct repeats in the border regions are involved in integration of T-DNA into plant DNA. That T-DNA having borders from two different Ti plasmids are less specifically integrated than are homologous borders supports this suggestion (G. Ooms et al. (1982) Plant Molec. Biol. 1:265–276).

N. S. Yadav et al. (1982) Proc. Natl. Acad. Sci. U.S.A. 79:6322–6326, have found a chi site, which in the bacteriophage λ augments general recombination in the surrounding DNA as far as 10 kilobases away, in a nopaline Ti plasmid just outside the left end of the T-DNA. R. B. Simpson et al. (1982) Cell 29:1005–1014, have not observed a chi sequence in an octopine Ti plasmid, though the possible range of action does not eliminate the possibility of one being necessary and present but outside of the region sequenced. The significance of the chi in the Ti plasmid is not known. If the chi has a function, it is probably used in Agrobacterium cells and not in the plants, as chi is not found within the T-DNA.

Agrobacterium—Manipulations of the TIP Plasmids

As detailed in the section on Shuttle Vectors, technology has been developed for the introduction of altered DNA sequences into desired locations on a TIP plasmid. Transposons can be easily inserted using this technology (D. J. Garfinkel et al. (1981) Cell 27:143–153). J.-P. Hernalsteen et al. (1980) Nature 287:654–656, have shown that a DNA sequence (here a bacterial transposon) inserted into T-DNA in the Ti plasmid is transferred and integrated into the recipient plant's genome. Though insertion of foreign DNA has been done with a number of genes from different sources, to date foreign genes have not usually been expressed under control of their own promoters. Sources of these genes include alcohol dehydrogenase (Adh) from yeast (K. A. Barton et al. (1983) Cell 32:1033–1043), AdhI (J. Bennetzen, unpublished) and zein from corn, interferon and globin from mammals, and the mammalian virus SV40 (J. Schell, unpublished). However, when the nopaline synthase gene was inserted into octopine T-DNA and transformed into plant tissue, it was found to be fully functional (C. L. Fink (1982) M.S. thesis, University of Wisconsin-Madison). The gene encoding phaseolin, the storage protein found in seeds he bean *Phaseolus vulgaris* L., has been transferred into and expressed in sunflower tumors. This latter work constitutes the first example of a transferred plant gene being expressed under control of its own promoter in foreign plant tissue. Transcription started and stopped at the correct positions, and introns were posttranscriptionally processed properly (T. C. Hall et al., U.S. application Ser. No. 485,613, which is hereby incorporated by reference). M. Holsters et al. (1982) Mol. Gen. Genet. 185:283–289, have shown that a bacterial transposon (Tn7) inserted into T-DNA could be recovered in a fully functional and seemingly unchanged form after integration into a plant genome.

Deletions can be generated in a TIP plasmid by several methods. Shuttle vectors can be used to introduce deletions constructed by standard recombinant DNA techniques (Cohen & Boyer, U.S. Pat. No. 4,237,224). Deletions with one predetermined end can be created by the improper excision of transposons (B. P. Koekman et al. (1979) Plasmid 2:347–357, and G. Ooms et al. (1982) Plasmid 7:15–29). J. Hille & R. Schilperoot (1981) Plasmid 6:151–154, have demonstrated that deletions having both ends at predetermined positions can be generated by use of two transposons. The technique can also be used to construct "recombinant DNA" molecules in vivo.

The nopaline synthase gene has been used for insertion of DNA segments coding for drug resistance that can be used to select for transformed plant cells. In plant cells, the kanamycin resistance gene from Tn5 is not transcribed under control of its own promoter (J. D. Kemp et al. (18 May 1982) Beltsville Symp. VII, Beltsville, Md., to be published (1983) in *Genetic Engineering: Applications to Agriculture*, ed. L. D. Owens; and C. L. Fink (1982) supra). M. W. Bevan et al. (1983) Nature 304:184–187 and R. T. Fraley et al. (1983) Proc. Natl. Acad. Sci. U.S.A. 80:4803–4807, have inserted the kanamycin resistance gene (neomycin phosphotransferase II) from Tn5 behind (i.e. under control of) the nopaline promoter. The construction was used to transform plant cells which in culture displayed resistance to kanamycin and its analogs such as G418. J. Schell et al. (18 Jan. 1983) 15th Miami Winter Symp. (see also J. L. Marx (1983) Science 219:830), reported a similar construction, in which the methotrexate resistance gene (dihydrofolate reductase) from Tn7 was placed behind the nopaline synthase promoter. Transformed cells were resistant to methotrexate. Similarly, L. Herrera-Estrella et al. (1983) Nature 303:209–213, have obtained expression in plant cells of enzymatic activity for octopine synthase and chloramphenicol acetyltransferase, an enzyme which in bacteria confers resistance to chloramphenicol, by placing the structural genes for these two enzymes under control of nos promoters.

T. C. Hall et al., U.S. application Ser. No. 485,614, which is hereby incorporated by reference, have fused the ocs promoter and the 5' end of the octopine synthase structural gene to the structural gene for the bean seed protein phaseolin. A fusion protein having the amino terminus of octopine synthase and lacking the amino terminus of phaseolin was produced under control of the T-DNA promoter. The introns, which were contributed by the phaseolin sequences, were posttranscriptionally processed properly.

A. J. de Framond et al. (1983) Biotechnol. 1:262–269, has reported that on the construction a "mini-Ti plasmid". In the nopaline T-DNA there is normally only one site cut by the restriction enzyme KpnI. A mutant lacking the site was constructed and a KpnI fragment, containing the entire nopaline T-DNA, was isolated. This fragment together with a kanamycin resistance gene was inserted into pRK290, thereby resulting in a plasmid which could be maintained in *A. tumefaciens* and lacked almost all non-T-DNA Ti sequences. By itself, this plasmid was not able to transform plant cells. However when placed in an *A. tumefaciens* strain containing an octopine Ti plasmid, tumors were induced which synthesized both octopine and nopaline. The mini-Ti plasmids has also been transferred into plant cells when complemented with a Ti plasmid deleted for its own T-DNA. These results indicated that the non-T-DNA functions acted in trans with T-DNA, that the missing nopaline Ti plasmid functions were complemented by the octopine Ti plasmid, and that the nopaline "mini-Ti" was functional in the transformation of plant cells. A similar pair of complementing plasmids, each containing either octopine T-DNA or onc genes, has been constructed by A. Hoekema et al. (1983) Nature , 303:179–180.

Chilton et al. (18 Jan. 1983) 15th Miami Winter Symp., also reported on the construction of a "micro-Ti" plasmid made by resectioning the mini-Ti with SinaI to delete essentially all of T-DNA but the nopaline synthase gene and the left and right borders. The micro-Ti was inserted into a modified pRK290 plasmid that was missing its SmaI site, and was employed in a manner similar to mini-Ti, with comparable results.

SUMMARY OF THE INVENTION

One object of this invention is to confer pest resistance, specifically insect resistance, to a plant. In pursuance of this goal, other objects are to stably insert a gene coding for an insecticidal protein into the genome of the plant cell, to have this gene expressed in plant tissues, for the expression to be either regulated or constitutive, and for the plant tissues to be in a normal plant. Another object is to provide novel specialized insecticidal tissues for a plant, in particular a means for producing on a normal dicot a gall which contains within tissue an insecticidal protein. Other objects and advantages will become evident from the following description.

The invention disclosed herein provides a plant comprising a genetically modified plant cell having an insecticide structural gene introduced and expressed therein under control of a plant expressible promoter. Further, the invention provides plant tissue comprising a plant cell whose genome includes T-DNA comprising an insecticide structural gene inserted in such orientation and spacing with respect to a plant expressible promoter as to be expressible in the plant cell under control of that promoter. Also provided are novel strains of bacteria containing and replicating T-DNA, as defined herein, the T-DNA being modified to contain an inserted insecticide structural gene in such orientation and spacing with respect to a plant expressible promoter as to be expressible in a plant cell under control of said promoter. Further, the invention provides novel plasmids having the ability to replicate in *E. coli* and comprising T-DNA, and further comprising an insecticide structural gene inserted within T-DNA contained within the plasmid, in such manner as to be expressible in a plant cell under control of a plant expressible promoter. Additionally, this invention discloses novel plasmids wherein the insecticide structural gene is capable of expression in *E. coli* or *Bacillus subtilis*, and furthermore discloses strains of bacteria harboring said bacterial expression plasmids.

The present invention comprises an insecticide structural gene under control of a promoter expressible in plant cells, said promoter/gene combination being inserted into a plant cell by any means known to the art. More specifically, in its preferred embodiment the invention disclosed herein further comprises expression in plant cells of an insecticide structural gene under control of a plant expressible promoter, after introduction via T-DNA, that is to say, by inserting the insecticide structural gene into T-DNA under control of a plant expressible promoter and introducing the T-DNA containing the insert into a plant cell using known means.

The invention is useful for genetically modifying plant tissues and whole plants by inserting useful insecticide structural genes from various bacterial species or strains. Such useful insecticide structural genes include, but are not limited to, the genes coding for insecticidal proteins as defined below, especially the crystal protein of *Bacillus thuringiensis*, related proteins, and the like. The invention is exemplified by introduction and expression of a structural gene for a crystal protein from *B. thuringiensis* var. *kurstaki* HD-73 into co,ton or tobacco plant cells. Once plant cells expressing an insecticide structural gene under control of a plant expressible promoter are obtained, plant tissues and whole plants can be regenerated therefrom using methods and techniques well known in the art. The regenerated plants are then reproduced by conventional means and the introduced genes can be transferred to other strains and cultivars by conventional plant breeding techniques.

The introduction and expression of the structural gene for an insecticidal protein can be used to protect a crop from infestation with insect larvae such as hornworm (Manduca sp.) or European corn borer (*Ostrinia nubilalis*). Other uses of the invention, exploiting the properties of other insecticide structural genes introduced into other plant species will be readily apparent to those skilled in the art. The invention in principle applies to any introduction of an insecticide structural gene into any plant species into which foreign DNA (in the preferred embodiment T-DNA) can be introduced and in which said DNA can remain stably replicated. In general these taxa presently include, but are not limited to, gymnosperms and dicotyledenous plants, such as sunflower (family Compositeae), tobacco (family Solanaceae), alfalfa, soybeans and other legumes (family Leguminoseae), cotton (family Malvaceae), and most vegetables. Pests which may be controlled by means of the present invention and the crops that may be protected frown them include, but are not limited to, those listed in Tables 1 and 2, respectively. Because of its susceptibility to a number of larvae, cotton is an ideal choice for the insertion of an insecticidal protein gene. Each of the following is a major cotton pest and is also susceptible to the *B. thuringiensis* insecticidal protein: *Heliothis zea* (cotton bollworm), *Pectionophora gossypiella* (pink bollworm), *Heliothis virescens* (tobacco budworm), *Trichoplusia ni* (cabbage looper). Application of insecticidal protein prepared from sporulating *B. thuringiensis* does not control insects such as the pink bollworm in the field because of their particular life cycles and feeding habits. A plant containing in its tissues insecticidal protein will control this recalcitrant type of insect, thus providing advantage over prior insecticidal uses of *B. thuringiensis*. By incorporation of the insecticidal protein into the tissues of a plant, the present invention additionally provides advantage over such prior uses by eliminating instances of nonuniform application and the costs of buying and applying insecticidal preparations to a field. Also, the present invention eliminates the need for careful timing of application of such preparations since small larvae are most sensitive to Insecticidal protein and the protein is always present, minimizing crop damage that would otherwise result from preapplication larval foraging.

BRIEF DESCRIPTION OF THE FIGURES

FIG. 1 presents the sequence of the crystal protein gene of p123/58–10, described in Example 1.

DETAILED DESCRIPTION OF THE INVENTION

Figure 2:
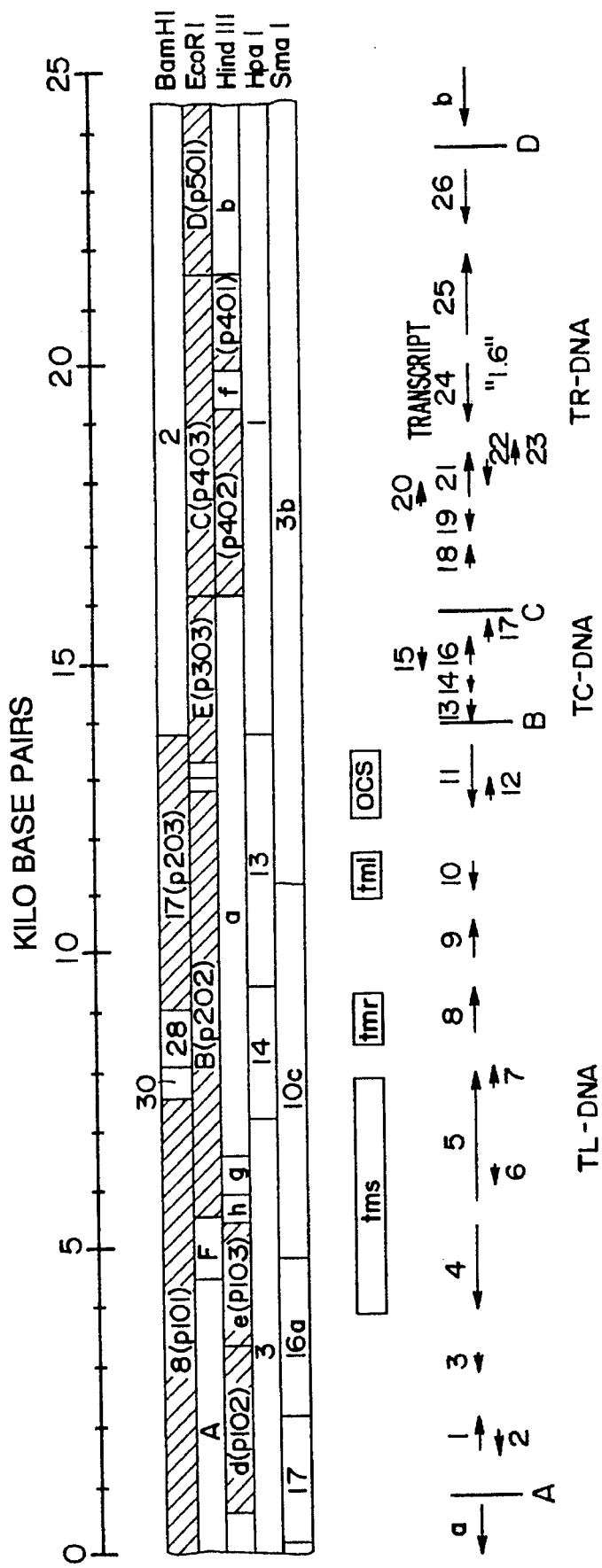
FIG. 2 presents a map of restriction sites and transcripts of the T-DNA of pTi15955.

The following definitions are provided, in order to remove ambiguities to the intent or scope of their usage in the specification and claims.

T-DNA: A segment of DNA derived from the transformation-inducing principle (TIP) which becomes integrated in the plant genome. As used herein, the term includes DNA originally derived from any tumor-inducing strain of Agrobacterium including *A. tumefaciens* and *A. rhizogenes*, the inserted segment of the latter sometimes referred to in the prior art as R-DNA. In addition, as used herein the term T-DNA includes any alterations, modifications, mutations, substitutions, insertions and deletions either naturally occurring or introduced by laboratory procedures, a principal structural requirement and limitation to such modifications being that sufficient of the right and left ends of naturally-occurring T-DNAs be present to insure the expected function of stable integration in the transformed plant cell genome which is characteristic of T-DNA. The T-DNA may itself be a composite of segments derived from a plurality of sources, naturally occurring or synthetic. In addition, the T-DNA must contain at least one plant expressible promoter, 5' or "upstream" from the site of insertion of the insecticide structural gene, in sufficiently complete form to control initiation of transcription and initiation of translation of an inserted insecticide structural gene. This promoter may be derived from a T-DNA gene, a plant gene, or any other gene having a promoter that is functional within a plant cell in at least one tissue and at least one developmental stage. Preferably, an insertion site will be provided "downstream" in the direction of transcription and translation initiated by the promoter (3' to the promoter), so located with respect to the promoter to enable an insecticide structural gene inserted therein to be expressed under control of the promoter, either directly or as a fusion protein. The T-DNA may also include a 3'-untranslated region downstream from the site of insertion of the insecticide structural gene, which may function to regulate termination of transcription, polyadenylation, and post-transcriptional RNA processing. Optionally, a fusion protein may also be formed between the insecticide structural gene and the 3' end of the structural gene donating the 3'-untranslated region. The promoter and 3'-untranslated region elements may be derived from the same, or different pre-existing genes and may be derived from the same or different plant, T-DNA, or other sources. For example, an insecticide structural gene, as exemplified herein, could be nested between a plant gene promoter and 3' sequence from the same gene, or it could be a construct comprising the 3'-untranslated region of one gene and the promoter of another, derived from the same or different plant species or T-DNA. The coding region of a plant gene, as herein defined, may include a cDNA copy of the structural portion of a plant gene. The promoter and 3'-untranslated regions may also include modifications, either naturally or artificially induced, and may include chemically synthesized segments.

Plant promoter:

As used herein includes regulatory elements, and may further include structural elements, of a plant gene said elements being exogenous to the genes of T-DNA itself. These include, but are not limited to, promoters of the genes for phaseolin and the small subunit of ribulose-1,5-bisphosphate carboxylase. Furthermore, a plant gene promoter is a region of the gene which provides for and may regulate the initiation of transcription and the initiation of translation. Additionally, the plant structural gene sequences (the region which codes for a protein in part or in whole and which may or may not contain one or more introns) may be introduced into T-DNA. (An intron is a region of a gene transcript which is posttranscriptionally removed before the mRNA is translated.) Expression under control of a plant promoter may take the form of direct expression in which the structural gene normally controlled by the promoter is removed in part or in whole and replaced by the inserted insecticide structural gene, a start codon being provided either as a remnant of the plant structural gene or as part of the inserted insecticide structural gene, or by fusion protein expression in which part or all of the plant structural gene is inserted in correct reading frame phase within the existing plant structural gene. In the latter case, the expression product is referred to as a fusion protein. The promoter segment may itself be a composite of segments derived from a plurality of sources, naturally occurring or synthetic. Sources of a plant promoter include, but are not limited to, plants listed in Table 2.

T-DNA promoter:

Refers to any of the naturally occurring promoters commonly associated with integrated T-DNA. These include, but are not limited to, promoters of the "1.6" transcript, octopine synthase gene (ocs), nopaline synthase gene (nos), tins, tml, and tmr genes, and may depend in part on the TIP source of the T-DNA. Expression under control of a T-DNA promoter may take the form of direct expression in which the structural gene normally controlled by the promoter is removed in part or in whole and replaced by the inserted insecticide structural gene, a start codon being provided either as a remnant of the T-DNA structural gene or as part of the inserted insecticide structural gene, or by fusion protein expression in which part or all of the plant structural gene is inserted in correct reading frame phase within the existing T-DNA structural gene. In the latter case, the expression product is referred to as a fusion protein. The promoter segment may itself be a composite of segments derived from a plurality of sources, naturally occurring or synthetic.

Plant expressible promoter:

As used herein includes the definitions for T-DNA promoter and plant promoter, supra. However, an essential aspect of the promoter component of the present invention is that the insecticide structural gene be under control of promoter expressible in a plant cell. Therefore, plant expressible promoter additionally refers to any promoter expressible in a plant cell which is expressed in at least one tissue during at least one developmental stage. Sources might include, but need not be limited to, plant viruses (e.g. the promoters for the 35S and 19S transcripts of cauliflower mosaic virus, CaMV), animal viruses, nonplant eukaryotes (e.g. animals, yeast), or plastids (e.g. a chloroplast or prokaryotic promoter if the insecticide gene is to be inserted into chloroplast DNA). Properties and components of a promoter that is derived from a source that is not a plant DNA or T-DNA (e.g. "TATA boxes", ATG translational start sites, intron splicing sites, etc.) are the same as described supra for T-DNA promoters and plant promoters are also included thin the present definition. The promoter segment may itself be a composite of segments derived from a plurality of sources, naturally occurring or synthetic.

Insecticide structural gene:

As used herein includes that portion of an insecticide gene comprising a DNA segment coding for an insecticidal protein, polypeptide or portion thereof, possibly including a translational start codon, but lacking other functional elements of a bacterial gene that regulate initiation of transcription and initiation of translation, commonly referred to as the promoter region. (Note that in the present invention such bacterial functional elements may be present after transfer of the insecticide structural gene into T-DNA. However, because they are not functional within a plant cell, such elements are not referred to by the tern "insecticide structural gene"). An insecticide structural gene may be derived in whole or in part from plasmid DNA, genomic DNA, cDNA and chemically synthesized DNA. It is further contemplated that an insecticide structural gene may contain one or more modifications in either the coding segments or untranslated regions which could affect the biological activity or chemical structure of the expression product, the rate of expression or the manner of expression control. Such modifications could include, but are not limited to, mutations, insertions, deletions, substitutions, and "silent" modifications that do not alter the chemical structure of the expression product but which affect intercellular localization, transport, excretion or stability of the expression product. The structural gene may constitute an uninterrupted coding sequence or it may include one or more introns, bounded by the appropriate plant functional splice junctions, which may be obtained from synthetic or a naturally occurring source. The structural gene may be a composite of segments derived from a plurality of sources, naturally occurring or synthetic, coding for a composite protein, the composite protein being insecticidal for being derived in part from an insecticidal protein.

Insecticidal protein:

As used herein includes a bacterial protein toxic in any way to insects. This includes a protein or peptide that is directly or indirectly toxic or growth inhibitory under any circumstances to any insect. This also includes proteins that are toxic upon contact, ingestion, or respiration, where alone or in combination with other material, at any time within the life cycle of an insect, including egg, larva, pupa, nymph, and adult stages. This includes proteins toxic to insects, especially those of the families Lepidoptera and Diptera, and those of the genera Ostrinia, Hellothis, Pectinophora, and Trichoplusia, e.g. *M. sexta, O. nubilalis, H. zea, H. virescens, P. gossypiella,* and *T. ni.* Other taxa that might be chosen as targets include, but are not limited to, those listed in Table 1. Examples of insecticidal proteins include, but are not limited to various varieties, listed in Table 3, of *Bacillus thuringiensis* or of other species of Bacillus, e.g. *B. cereus, B. popilliae,* and *B. sphaericus.* Genes that are used to construct or otherwise encode sequences encoding proteins toxic to insects include, but are not limited to, phospholipases, hyaluronidases, phosphatrsses, proteases, and the various crystal proteins of *B. thuringiensis.* The term crystal protein should be understood to refer to both the protoxin and toxin forms, to toxic proteins related to the protein which is found in the crystalline inclusion bodies of *Bacillus thuringiensis,* and to artificial modifications of naturally occuring crystal proteins. Related proteins might be identified by nucleic acid or protein structural or sequence homology, immunological cross-reactivity, or cross-hybridization of nucleic acids.

Plant tissue:

Includes differentiated and undifferentiated tissues of plants including, but not limited to roots, shoots, pollen, seeds, tumor tissue, such as crown galls, and various forms of aggregations of plant cells in culture, such as embryos and calluses. The plant tissue may be in planta or in organ, tissue, or cell culture, and may be derived from plants which include, but are not limited to, those listed in Table 2.

Plant cell:

As used herein includes plant cells in planta and plant cells and protoplasts in culture, and may be derived from plants which include, but are not limited to those listed in Table 2.

Production of a genetically modified plant expressing an insecticide structural gene introduced via T-DNA combines the specific teachings of the present disclosure with a variety of techniques and expedients known in the art. In most instances, alternatives expedients exist for each stage of the overall process. The choice of expedients depends on variables such as the choice of the basic TIP or other vector systems for the introduction and stable maintenance of the expressible insecticide structural gene, the plant species to be modified and the desired regeneration strategy, and the particular insecticide structural gene to be used, all of which present alternative process steps which those of ordinary skill are able to select and use to achieve a desired result. For instance, although the starting point for obtaining an insecticide structural gene is exemplified in the present application by DNA isolated from *B. thuringiensis* var. *kurstaki* HD-73, DNA of other insecticidal protein gene-carrying bacterial strains or recombinant DNA molecules might be substituted as long as appropriate modifications are made to the gene isolation and manipulation procedures. As novel means are developed for the controlled expression and/or stable insertion of foreign genes in plant cells, those of ordinary skill in the art will be able to select among those alternate process steps to achieve a desired result. The fundamental aspects of the invention are the nature and structure of the insecticide structural gene and its means of insertion and expression in a plant genome. The remaining steps of the preferred embodiment for obtaining a genetically modified plant include inserting the promoter/insecticide structural gene combination into T-DNA transferring the modified T-DNA to a plant cell wherein the modified T-DNA becomes stably integrated as part of the plant cell genome, techniques for in vitro culture and eventual regeneration into whole plants, which may include steps for selecting and detecting transformed plant cells and steps of transferring the introduced gene from the originally transformed strain into commercially acceptable cultivars.

A principal feature of the present invention in its preferred embodiment is the construction of T-DNA having an inserted insecticide structural gene under control of a plant expressible promoter, or, most preferably, a T-DNA promoter, as these terms have been defined, supra. The insecticide structural gene must be inserted in correct position and orientation with respect to the desired promoter. Position has two aspects. The first relates to which side of the promoter the structural gene is inserted. It is known that the majority of promoters control initiation of transcription and translation in one direction only along the DNA. The region of DNA lying under promoter control is said to "downstream" or alternatively "behind" or "3' to" the promoter. Therefore, to be controlled by the promoter, the correct position of plant structural gene insertion must by "downstream" from the promoter. (It is recognized that a few known promoters exert bidirectional control, in which case either side of the promoter could be considered to be "downstream" therefrom.) The second aspect of position refers to the distance, in base pairs, between known functional elements of the promoter, for example the transcription initiation site, and the translational start site of the structural gene. Substantial variation appears to exist with regard to this distance, from promoter to promoter. Therefore, the structural requirements in this regard are best described in functional terms. As a first approximation, reasonable operability can be obtained when the distance between the promoter and the inserted insecticide structural gene is similar to the distance between the promoter and the T-DNA gene it normally controls. Orientation refers to the directionality of the structural gene. That portion of a structural gene which ultimately codes for the amino terminus of the plant protein is teemed the 5' end of the structural gene, while that end which codes for amino acids near the carboxyl end of the protein is termed the 3' end of the structural gene. Correct orientation of the insecticide structural gene is with the 5' end thereof proximal to the promoter. An additional requirement in the case of constructions leading to fusion protein expression is that the insertion of the insecticide structural gene into the promoter-donated structural gene sequence must be such that the coding sequences of the two genes are in the same reading frame phase, a structural requirement which is well understood in the art. An exception to this requirement, of relevance to the present invention, exists in the case where an intron separates coding sequences derived from an insecticidal protein gene from the first coding segment of the insecticide structural gene. In that case, the insecticide structural gene must be provided with a splice site compatable with the upstream splice junction contributed by the noninsecticidal coding sequences, and the intron splice sites must be so positioned that the correct reading frame for the promoter-donated structural gene and the insecticide structural gene are restored in phase after the intron is removed by post-transcriptional processing. Differences in rates of expression or developmental control may be observed when a given insecticide structural gene is inserted under control of different plant expressible promoters. Different properties, including, but not limited to such properties as stability, intercellular or intracellular localization or excretion, solubility, target specificity, and other functional properties of the expressed protein itself may be observed in the case of fusion proteins depending upon the insertion site, the length and properties of the segment of T-DNA protein included within the fusion protein and mutual interactions between the components of the fusion protein that effect folded configuration thereof, all of which present numerous opportunities to manipulate and control the functional properties of the insecticidal protein product, depending upon the desired physiological properties within the plant cell, plant tissue, and whole plant.

Location of the promoter/insecticide structural gene combination insertion site is not critical as long as the transfer function of sequences immediately surrounding the T-DNA borders are not disrupted, since these regions appear from prior art studies to be essential for insertion of the modified T-DNA into the plant genome. Preferred insertion sites are those which lie in areas that are most actively transcribed, in particular the tml gene and an area designated "1.6" lying in the HindIII-f fragment, and equivalent to transcript 24, as shown in FIG. 2. The term "1.6" is used herein to designate this actively transcribed region of T-DNA. The T-DNA into which the promoter/insecticide gene combination is inserted, is obtained from any of the TIP plasmids. The insecticide gene is inserted by standard techniques well known to those skilled in the art. The orientation of the inserted plant gene, with respect to the direction of transcription and translation of endogenous T-DNA genes is not critical, either of the two possible orientations is functional. Differences in rates of expression may be observed when a given gene is inserted at different locations within T-DNA, possibly because of such factors as DNA methylation and chromatin structure. Readily detectable levels of expression of a plant promoter from the phaseolin gene have been obtained where that gene was inserted into pTi15955, an octopine-type plasmid of *A. tumefaciens* at a SmaI site found within the tml gene or a HpaI site found within tmr.

A convenient means for inserting a promoter/insecticide structural gene combination into T-DNA involves the use of a shuttle vector, as described supra, having segments of T-DNA (those segments between which insertion is desired) incorporated into a plasmid capable of replacing in *E. coli*. The T-DNA segment contains a restriction site, preferably one which is unique within the shuttle vector. The insecticide structural gene can be inserted at the unique site in the T-DNA sequences and the shuttle vector is transferred into cells of the appropriate Agrobacterium strain, preferably one whose T-DNA is homologous with the T-DNA segments of the shuttle vector. The transformed Agrobacterium strain is preferably grown under conditions which permit selection of a double-homologous recombination event which results in replacement of a pre-existing segment of the Ti plasmid with a segment of T-DNA of the shuttle vector, However, it should be noted chat the present invention is not limited to the introduction of the promoter/insecticide structural gene combination into T-DNA by a double homologous recombination mechanism; a homologous recombination event with a shuttle vector (perhaps have only a single continuous region of homology with the T-DNA) at a single site or an insertion of a promoter/gene-carrying bacterial transposon will also prove an effective means for inserting that combination into T-DNA.

Following the strategy just described, the modified T-DNA can be transferred to plant cells by any technique known in the art. For example, this transfer is most conveniently accomplished either by direct infection of plants with the novel Agrobacterium strain containing an insecticide gene incorporated within T-DNA, or by cocultivation of the Agrobacterium strain with plant cells. The former technique, direct infection results in due course in the appearance of a tumor mass or crown gall at the site of infection. Crown gall cells can be subsequently grown in culture and, under appropriate circumstances known to those of ordinary skill in the art, regenerated into whole plants that contain the inserted T-DNA segment. Using the method of cocultivation, a certain proportion of the plant cells are transformed, that is to say have T-DNA transferred therein and inserted in the plant cell genome. In either case, the transformed cells must be selected or screened to distinguish them from untransformed cells. Selection is most readily accomplished by providing a selectable marker incorporated into the T-DNA in addition to the insecticide structural gene. Examples include either dihydrofolate reductase or neomycin phosphotransferase expressed under control of a nopaline synthase promoter. These markers are selected by growth in medium containing methotrexate or kanamycin, respectively, or their analogs. In addition, the T-DNA provides endogenous markers such as the gene or genes controlling hormone-independent growth of Ti-induced tumors in culture, the gene or genes controlling abnormal morphology of Ri-induced tumor roots, and genes that control resistance to toxic compounds such as amino acid analogs, such resistance being provided by an opine synthase. Screening methods well known to those skilled in the art include assays for opine production, specific hybridization to characteristic RNA or T-DNA sequences, or immunological assays for specific proteins, including ELISAs (acronym for "enzyme linked immunosorbant assay"), radioimmune assays and "western" blots. Additionally tile toxic properties of expressed insecticidal protein can be used to identify transformed tissue.

An alternative to the shuttle vector strategy involves the use of plasmids comprising T-DNA or modified T-DNA, into which an insecticide structural gene is inserted, said plasmids being capable of independent replication in an Agrobacterium strain. Recent evidence reviewed in the Background indicates that the T-DNA of such plasmids can be transferred from an Agrobacterium strain to a plant cell provided the Agrobacterium strain contains certain trans-acting genes whose function is to promote the transfer of T-DNA to a plant cell. Plasmids that contain T-DNA and are able to replicate independently in an Agrobacterium strain are herein termed "sub-TIP" plasmids. A spectrum of variations is possible in which the sub-TIP plasmids differ in the amount of T-DNA they contain. One end of the spectrum retains all of the T-DNA from the TIP plasmid, and is sometimes termed a "mini-TIP" plasmid. At the other end of the spectrum, all but the minimum amount of DNA surrounding the T-DNA border is deleted, the remaining portions being the minimum necessary to be transferrable and integratable in the host cell. Such plasmids are termed "micro-TIP". Sub-TIP plasmids are advantageous in that they are small and relatively easy to manipulate directly, eliminating the need to transfer the gene to T-DNA from a shuttle vector by homologous recombination. After the desired structural gene has been inserted, they can easily be introduced directly into a plant cell containing the trans-acting genes that promote T-DNA transfer. Introduction into an Agrobacterium strain is conveniently accomplished either by transformation of the Agrobacterium strain or by conjugal transfer from a donor bacterial cell, the techniques for which are well known to those of ordinary skill. For purposes of introduction of novel DNA sequences into a plant genome, TIP plasmids and sub-TIP plasmids should be considered functionally equivalent.

Although the preferred embodiment of this invention incorporates a T-DNA-based Agrobacterium-mediated system for incorporation of the insecticide gene into the genome of the plant which is to be made insect resistant, other means for transferring and incorporating the gene are also included within the scope of this invention. Other means for the stable incorporation of the insecticide gene into a plant genome additionally include, but are not limited to, use of vectors based upon viral genomes, minichromosomes, transposons, and homologous or nonhomologous recombination into plant chromosomes. Alternate forms of delivery of these vectors into a plant cell additionally include, but are not limited to, direct uptake of nucleic acid, fusion with vector-containing liposomes, microinjection, and encapsidation in viral coat protein followed by an infection-like process. System based on Agrobacterium cells and TLPs can be used to transform dicots and gymnosperms by transfer of DNA from a bacterium to a plant cell; system based on alternate vectors or means for vector delivery may be used to transform all gymnosperms and all angiosperms, including both monocots and dicots.

Regeneration of transformed cells and tissues is accomplished by resort to known techniques. An object of the regeneration step is to obtain a whole plant that grows and reproduces normally but which retains integrated T-DNA. The techniques of regeneration vary somewhat according to principles known in the art, depending upon the origin of the T-DNA, the nature of any modifications thereto and the species of the transformed plant. Plant cells transformed by an Ri-type T-DNA are readily regenerated, using techniques well known to those of ordinary skill, without undue experimentation. Plant cells transformed by Ti-type T-DNA can be regenerated, in some instances, by the proper manipulation of hormone levels in culture. Preferably, however, the Ti-transformed tissue is most easily regenerated if the T-DNA has been mutated in one or both of the tmr and tms genes. Inactivation of these genes returns the hormone balance in the transformed tissue towards normal and greatly expands the ease and manipulation of the tissue's hormone levels in culture, leading to a plant that is readily regenerated because of its more normal hormone physiology. It is important to note that if the mutations in tmr and tms are introduced into T-DNA by double homologous recombination with a shuttle vector, the incorporation of the mutation must be selected in a different manner than the incorporation of the promoter/ insecticide structural gene. For example, in the former instance one might select for chloramphenicol resistance while the latter selection might be for resistance to kanamycin. The inactivation of the tms and tmr loci may be accomplished by an insertion, deletion, or substitution of one or more nucleotides within the coding regions or promoters of these genes, the mutation being designed to inactivate the promoter or disrupt the structure of the protein. (The construction of suitable mutations has been exemplified by T. C. Hall et al., Ser. Nos. 485,613 and 485,614.) In some instances, tumor cells are able to regenerate shoots which carry integrated T-DNA and express T-DNA genes, such as nopaline synthase, and which also express an inserted plant structural gene. The shoots can be maintained vegetatively by grafting to rooted plants and can develop fertile flowers. The shoots thus serve as parental plant material for normal progeny plants carrying T-DNA and expressing the plant structural gene inserted therein.

The genotype of the plant tissue transformed is often chosen for the ease with which its cells can be grown and regenerated in in vitro culture. Should a cultivar of agronomic interest be unsuitable for these manipulations, a more amenable variety is first transformed. After regeneration, the newly introduced foreign insecticidal protein gene is readily transferred to the desired agronomic cultivar by techniques well known to those skilled in the arts of plant breeding and plant genetics. Sexual crosses of transformed plants with the agronomic cultivars yielded initial hybrid. These hybrids can then be back crossed with plants of the desired genetic background. Progeny are continuously screened and selected for the continued presence of integrated T-DNA or for the new phenotype resulting from expression of the inserted insecticidal protein gene. In this manner, after a number of rounds of back crossing and selection, plants can be produced having a genotype essentially identical to the agronomically desired parents with the addition of the inserted insecticidal protein gene.

In an alternative method for conferring insect resistance to a crop, one may infect plants within a field which is to be protected with an Agrobacterium cell harboring a TIP plasmid having undisabled T-DNA which carries an expressible insecticidal protein gene. We have found that larvae will feed on crown gall tissue. When insect larve infesting the field eat transformed tissue containing an insecticide gene, they will be affected by the insecticidal protein within that tissue. The Agrobacterium and TIP might additionally encode genes for insect attractants. The presence of such attractants in transformed tissue will increase the insects preference of such tissue as a food source relative to the rest of the crop material in the field.

EXAMPLES

The following Examples utilize techniques well known and accessible to those skilled in the arts of molecular biology and manipulation of TIPs and Agrobacterium; such methods are fully described in one or more of the cited references if not described in detail herein. Enzymes are obtained from commercial sources and are used according to the vendor's recommendations or other variations known to the art. Reagents, buffers and culture conditions are also known to those in the art. Reference works containing such standard techniques include the following: R. Wu, ed. (1979) Meth. Enzymol. 68, R. Wu et al., eds. (1983) Meth. Enzymol. 100 and 101, L. Grossman & K. Moldave, eds. (1980) Meth. Enzymol. 65, J. H. Miller (1972) *Experiments in Molecular Genetics*, R. Davis et al. (1980) *Advanced Bacterial Genetics*, R. F. Schleif & P. C. Wensink (1982) *Practical Methods in Molecular Biology*, and T. Maniatis et al. (1982) *Molecular Cloning*. Additionally, R. F. Lathe et al. (1983) Genet. Engin. 4:1–56, make useful comments on DNA manipulations.

Textual use of the name of a restriction endonuclease in isolation, e.g. "BclI", refers to use of that enzyme in an enzymatic digestion, except in a diagram where it can refer to the site of a sequence susceptible to action of that enzyme, e.g. a restriction site. In the text, restriction sites are indicated by the additional use of the word "site", e.g. "BglI site". The additional use of the word "fragment", e.g. "BglI fragment", indicates a linear double-stranded DNA molecule having ends generated by action of the named enzyme (e.g. a restriction fragment). A phrase such as "BclI/SmaI fragment" indicates that the restriction fragment was generated by the action of two different enzymes, here BclI and SmaI, the two ends resulting from the action of different enzymes. Note that the ends will have the characteristics of being "blunt" or "sticky" (i.e. having a single-stranded protuberance capable of base-pairing with a complementary single-stranded oligonucleotide) and that the sequence of a sticky-end will be determined by the specificity of the enzyme which produces it.

In these Examples, special symbols are used to make sequences more easily understood. Sequences that code for proteins are underlined, and codons are separated with slashes (/). The positions of cuts or gaps in each strand caused by restriction endonucleases or otherwise are indicated by the placement of asterisks (*).

Plasmids, and only plasmids, are prefaced with a "p", e.g., pTi15955 or pKS-4, and strain parenthetically indicate a plasmid harbored within, e.g., *A. tumefaciens* (pTi15955) or K802(pKS-4). Table 4 provides an index useful for identifying plasmids and their interrelationships. Table 5 provides a list of deposited strains.

Example 1

The first step in developing an insect resistant crop was to clone the insecticidal protein gene of *B. thuringiensis* var. *kurstaki* HD-73, which is on deposit with the Agricultural Research Culture Collection, Northern Regional Research Laboratory, Peoria, Ill. and has NRRL number B-4488.

1.1 Cloning the *Bacillus thuringiensis* insecticidal protein gene

The 50 megadalton (MD) plasmid was enriched from HD-73 using sucrose gradient centrifugation. A HD-73 library was constructed by first digesting this plasmid with HindIII. The resulting fragments were mixed with and ligated to HindIII-linearized pBR322 (F. Bolivar et al. (1978) Gene 2:95–113) and transformed into *E. coli* HB101. Ampicillin-resistant tetracycline-sensitive transformants were screened by digesting isolated plasmid DNA with HindIII and choosing those clones with 6.6 kilobase pair (kbp) inserts. Colonies containing plasmids p123/58-3 and p123/58-10 were selected from the HD-73 library for further analysis using an insect bioassay (see Example 8). These clones were grown in L-broth and a 250 fold concentrated cell suspension was sonicated and the extract applied to the surface of insect diet. Neonatal *Manduca sexta* (tobacco hornworm) larvae were placed on the diet for one week. Insect larvae fed extracts of strains harboring p123/58-3 or p123/58-10 did not grow and all larvae died in 2 to 5 days. There was no apparent difference between the larvae fed these extracts and those fed insecticidal protein purified from cells of *B. thuringiensis*.

Restriction enzyme analysis of p123/58-3 and p123/58-10 showed that the two plasmids were identical except for having the 6.6 kbp *B. thuringiensis* DNA fragment inserted into the pBR322 vector in opposite orientations. Note that either of these two plasmids can be converted to the other by digestion with HindIII, religation, and transformation into HB101 followed by appropriate selection and screening steps.

p123/58-10 was used to further probe the transformation from the HD-73 plasmid library. Sixteen of the 572 colonies hybridized to the insert of clone p123/58-10 and all had the characteristic 6.6 kbp HindIII fragment. Further restriction enzyme analysis showed these clones to all be one of the two possible orientations in pBR322 of the same DNA fragment. This suggested there could be a single crystal protein gene in strain HD-73. That these clones represent the only insecticidal protein gene in HD-73 was confirmed by hybridizing labeled p123/58-10 probe to Southern blots of HD-73 plasmid DNA digested with HindIII, BglII or SalI. None of these enzymes has a restriction site in our cloned crystal protein gene. Hybridization results showed a single band of *B. thuringiensis* cellular DNA hybridized with p123/58-10 and further indicated that HD-73 has a single insecticidal crystal protein gene. We have identified a number of other clones by hybridization with a probe made from p123/58-10. Restriction mapping has shown that these clones are all identical to either p123/58-3 or p123/58-10, further supporting the conclusion that the HD-73 has a single crystal protein gene.

1.2 Immunological analysis

Analyses on the protein produced in the *E. coli* clones shows that p123/58-3 and p123/58-10 encoded-protein that formed a precipitin band with antiserum to *B. thuringiensis* insecticidal protein in Ouchterlony diffusion slides. Cell extracts were analyzed on 10% SDS-poly-acrylamide gels, transferred to nitrocellulose, and immunological reactions done with antibody and $^{125}$I-protein A (Western blots, Example 7). No band was found at 130 kD (kilodalton) where denatured protoxin is observed, however, a peptide of about 67 kD was seen that binds crystal protein antibody (Western blots done as in Example 7), and was identical in size to activated toxin. This peptide accounted for approximately 0.1% of the total *E. coli* protein.

1.3 Sequence analysis

Figure 1C:
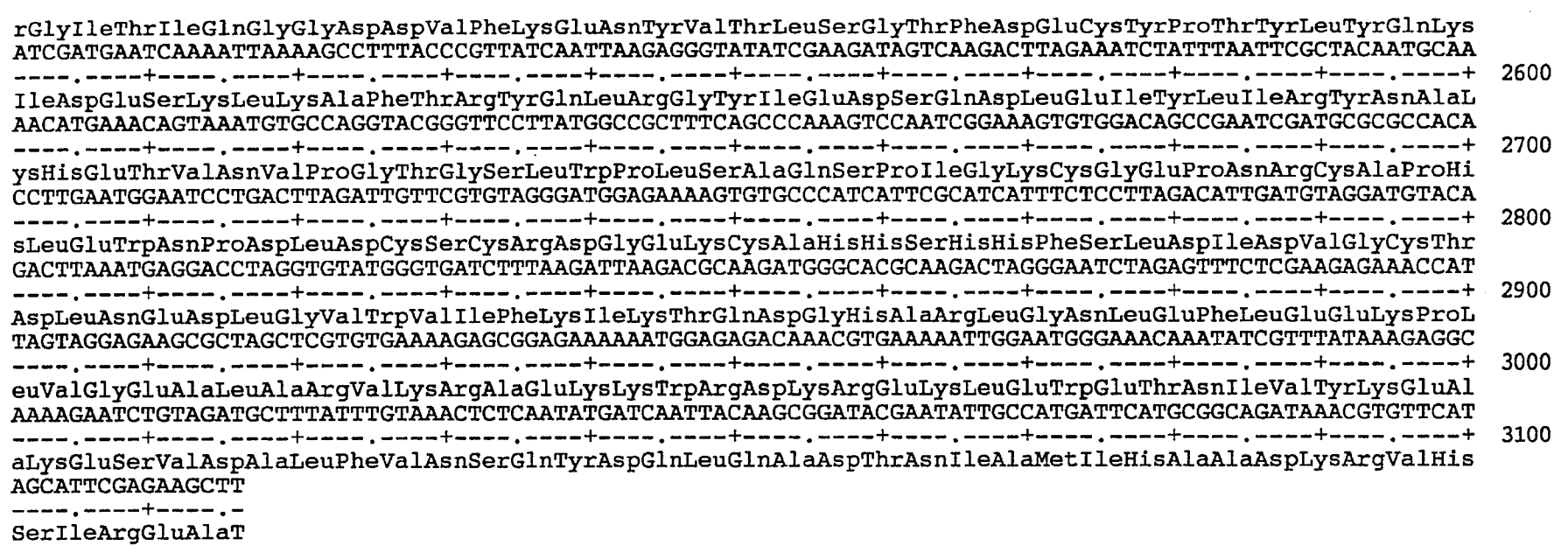

We compared our DNA sequence results (FIG. 1), obtained by methods well known to those skilled in the art of DNA sequencing (e.g. see A. M. Maxam & W. Gilbert (1980) Meth. Enzymol. 65:499–560), with published sequences (see Background). The published sequences showed only partial homology with our own sequence. An open reading frame of about 2.8 kbp was observed which was bounded at the 5'-end by a translational start signal (ATG) and did not stop before encountering the HindIII site at the junction between the B. thuringiensis DNA and the pBR322 vector. The size of the protein encoded by this open reading frame from the ATG to the HindIII site is greater than that of the 67 kD protein that we obtained to be translated in E. coli cells but less than what is needed to encode the 130 kD native crystal protein. That the exact means of translational termination in the pBR322 encoded read-thru peptide was not important was suggested by the finding that insecticidal activity was encoded by B. thuringiensis DNA inserts having either orientation within the pBR322 vector. Presumably the initially translated amino acid residues carboxy-terminal to the ultimate carboxy-terminus of the translated polypeptide were removed in E. coli by a proteolytic process similar to that which naturally activates the crystal protein.

Example 2

This example teaches the insertion of the *Bacillus thuringiensis* insecticide gene between a T-DNA gene promoter and a polyadenylation (poly(A) addition) signal, the transfer of the insecticide gene to various plant species via a Ti plasmid, and the regeneration of plants expressing this gene under control of the T-DNA promoter. A large part of the strategy used in this construction is diagramed in FIG. 3, which represents plasmids schematically and is not necessarily drawn to scale.

2.1 Introduction of BamHI site into the insecticidal protein gene

A BamHI site is introduced into the insecticidal protein gene of p123/58-10 at a location just 5' to the start of the coding sequence. The wild type base sequence (b) and the changed bases in an oligonucleotide primer (a) are as follows:

```
                    BamHI
a)  5' AGATGGAG*GATCCTT ATG GAT AAC AAT  3'
b)  ...AGATGGAG GTAACTT/ATG/GAT/AAC/...
                        Met Asp Asn Asn
```

The changed bases are the underlined ATC sequence in (a). Note that good hybridization properties are insured because only three out of 27 base-pairs are changed.

p123/58-10 is digested with HindIII and is mixed with and ligated to HindIII-linearized mWB2344 RF (replicative form) DNA. The mixture transformed into JM103 and transformed colonies are screened by plasmids isolation followed by restriction analysis for the presence of insertion of a single copy of she insecticidal protein gene-bearing fragment. Vectors containing the two possible orientations are labeled M13-Bt-A and M13-Bt-S. They have the anti-sense and sense strands, respectively, of the insecticide structural gene when in viral form.

M13-Bt-A is hybridized with the oligonucleotide primer, 5'AGATGGAGGATCCTTATGGATAACAAT3', previously synthesized as described in Example 10.1. The oligonucleotide: M13-Bt-A hybrid is incubated with the Klenow fragment of *E. coli* DNA polymerase I, covalently closed circular DNA (cccDNA) is enriched, and the mixture is transformed into JM103. The virions produced by transformants are isolated and used to infect cells at a low multiplicity of infection. RF DNA is isolated from a number of the infected colonies and is characterized by restriction mapping. Clones derived from the mutant oligonucleotide-primed strand are identified by the presence of a novel BamHI site at the 5'-end of the insecticide structural gene, and one such vector is designated M13-Bt-A(Bam).

M13-Bt-A(Bam) RF DNA is digested with BamHI and HindIII, and is mixed with arid ligated to a linker, synthesized as described in Example 10.1, having the following structure:

```
HindIII              BamHI
5'AGCTAGCTGACTAG3'
      3'TCGACTGATCCTAG5'
```

Note that this linker contains translational stop signals (underlined) in all three possible reading-phases. The linkers are trimmed by digestion with BamHI and an insecticide structural geese-bearing DNA fragment is purified by agarose gel electrophoresis.

2.2 Construction and modification of a promoter vehicle

The T-DNA "1.6" gene is summarized as follows:

```
          ClaI            960 bp   250 bp   ClaI   60 bp        50 bp
5'...TACACCAAAT*CG/ATG/GAC/ATG/..../TGA/.....AT*CGAT.....AAATAA....AAATAA.
..3'
   promoter          M   D   M .....stop     polyadenylation signals
```

By removing the ClaI fragment, the promoter region of the "1.6" gene can brought next to the 3'-downstream region of the gene. This 3' region includes polyadenylation signals. The resulting structure is summarized as follows:

```
                  ClaI              60 bp         50 bp
5'...ATACACCAAAT*CGATAGT..........AAATAA..........AAATAAAA...3'
    promoter                      polyadenylation signals
``` pKS111, which is a pRK290 clone corresponding to the T-DNA clone p403 (which encodes the "1.6" gene which was described in the Detailed Description, transcript 24 in FIG. 2, see also C. F. Fink (1982) M.S. thesis, University of Wisconsin-Madison), is digested with ClaI and then religated. (Alternatively, these same manipulations as described here can be done directly on p403, which is a pBR322-based clone, substituting ampicillin for tetracycline during selection.) The ligation mix is transformed into E. coli K802 (W. B. Wood (1966) J. Mol. Biol. 16:118) and selected for tetracycline resistance. Plasmids are isolated by doing "minipreps" (Plasmid preparations from small volume cell cultures) and restriction maps are obtained to prove the structure. The new vehicle, pKS-proI (see T. C. Hall et al., U.S. application Ser. No. 485,614), can be linearized by ClaI.

pKS-proI grown in K802 was cut with ClaI mixed with and ligated to a BamHI/ClaI linker having no 5'-phosphate, 5'CGGATC3'. The resulting mixture was digested with ClaI to remove religated pKS-proI, and transformed into K802. Plasmids from tetracycline resistant transformants are screened by restriction analysis and a plasmid having the ClaI site at the ATG translational start replaced with a BamHI site is designated pKS-proI(Bam).

2.3 Introduction of a Kanamycin Resistance Gene into pKS-proI(Bam)

It is advantageous to have a kanamycin resistance (kan) gene inserted next to the promoter/insecticide gene combination so as to allow selection of double homologous recombinants after a triparental mating. The source of kan was pKS-4 (Example 2.5). In pKS-4 the kan gene is flanked on one side by a ClaI site. In order to remove a kan gene bearing fragment from pKS-4 with ClaI (i.e. on a "ClaI/kan" fragment) it is necessary to introduce a ClaI site into that plasmid on the opposite side of kan from the existing ClaI site. This is accomplished by converting a conveniently positioned BamHI site (5' . . . G*GATCC . . . 3') to the specificity of ClaI (5' . . . AT*CGAT . . . 1').

pKS-4 is linearized by digestion with BamHI, thereby generation sticky-ends having the following structures:

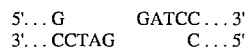

The recessed ends of this structure is filled in by incubation with the Klenow fragment of E. coli DNA polymerase I, forming the following blunt-ends:

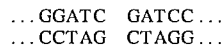

When these ends were blunt end ligated together, the resulting suture has the following sequence:

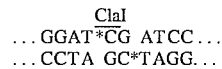

Note that the resulting structure is susceptible to the action of ClaI but not to that of BamHI.

Alternatively to the above construction, one may convert the BamHI site, or another conveniently located restriction site, into a ClaI site by use of the appropriate linkers. pKS-4 was digested with SmaI mixed with and ligated to ClaI/ blunt-ended linkers having the sequence 5'CATCGATG3', digested with ClaI, religated, and transformed into K802. Plasmids isolated from transformants resistant to kanamycin were screened for presence of a novel ClaI site in the position formally occupied by a Sinai site. A ClaI/kan fragment can be isolated from such a plasmid.

Figure 3:
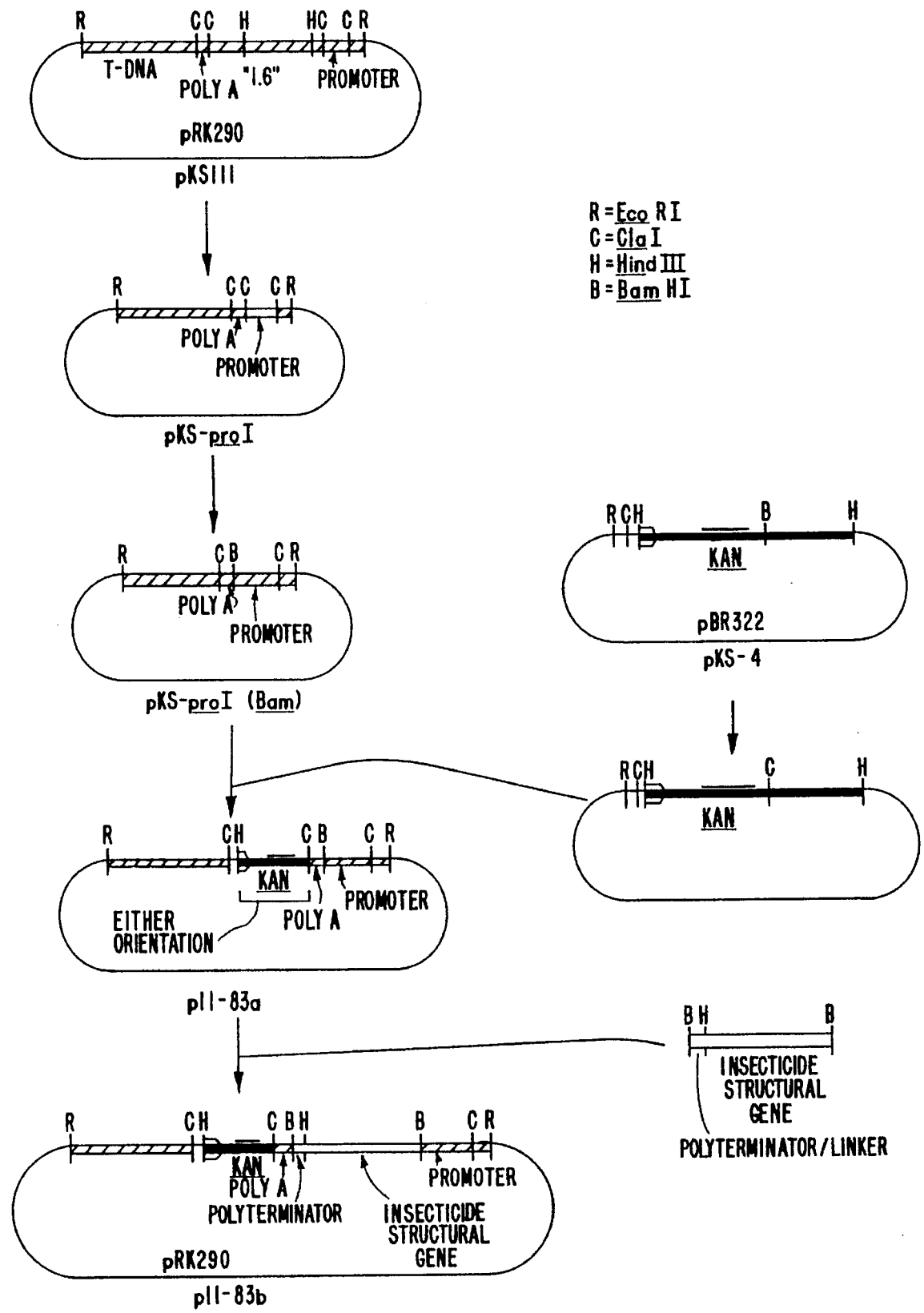
FIG. 3 is a diagram of a construction described in Example 2 of a recombinant DNA vector carrying an insecticide structural gene under control of a plant expressible promoter.

When grown in E. coli K802, pKS-proI(Bam) is methylated at two remaining ClaI sites: one is about 145 bases from the the promoter-polyadenylation junction (this is about 30 bases past the second polyadenylation site), the other is about 200 bases from the right hand p403 EcoRI site (see FIG. 2). Methylation blocks cutting by the ClaI restriction endonuclease at an otherwise susceptible site. Therefore, these methylations protect these sites and effectively direct action of the ClaI enzyme to other sites. pKS-proI-(Bam) is transferred to and grown in E. coli GM33, a strain that does not methylate adenosine residues in DNA, so that; the otherwise methylated ClaI sites can be cut. After purification of that plasmid from GM33 (pKS-proI(Bam)), a partial digestion is done with ClaI and the resulting mixture is ligated with the ClaI/kan fragment described above. After transformation into E. coli K802, transformants are selected on tetracycline and kanamycin containing media. After plasmid isolation and restriction mapping, a clone having the desired construction is identified and the plasmid found in this clone is labeled p11-83a (FIG. 3).

p11-83a has a kan gene-bearing fragment ligated into the "middle" ClaI site about 30 bp past the second polyadenylation site. The BamHI fragment of the insecticide gene, isolated from the modified vector constructed in Example 2.1, is now ligated into the BamHI site of BamHI-linearized p11-83a that has been transferred to and grown in K802 and is methylated. After transformation into K802, tetracycline and kanamycin selection, plasmid isolation, and restriction enzyme mapping, the desired construction having the insecticide structural gene inserted between the pti15955 "1.6" promoter and polyadenylation site is identified, and the plasmid harbored therein is labeled p11-83b (FIG. 3).

2.4 Introduction of p11-83b into Ti Plasmids p11-83b is introduced into pti15955, pTiA66 (equivalent to pti15955 but having a nonfunctional tms gene), and mutants deleted in gene affecting regeneration by homologous recombination (Example 10). Tobacco plants are transformed by a system described in Example 6, and transformants are identified by Southern and Northern blots (techniques well known to those skilled in the art) with appropriate probes and by the presence of octopine and crystal protein. Transformed tobacco tissue is lethal to tobacco hornworms. Tobacco plants are regenerated from transformed cells as described in Example 6, and entered into breeding programs. Fields of regenerated plants and their insecticidal protein-containing decendants are resistant to infestation by larve of insects such as tobacco hornworm by virtue of the toxic effect such larvae experience when eating tissue from such plants.

2.5 Cloning and isolation of a kanamycin resistance gene pRZ102 (R. A. Jorgenson et al. (1979) Mol. gen. Genet. 177:65–72), a ColE1 plasmid carrying a copy of the transposon Tn5, was digested with BamHI and HindIII, mixed with pBR322 previously linearized with the same two enzymes, ligated, and transformed into K802. Plasmids, isolated from transformants selected for resistance to both ampicillin and kanamycin were restriction mapped and one having the structure shown in FIG. 3 was labeled pKS-4.

Example 3

This example teaches another method of inserting an expressible gene for the *B. thuringiensis* insecticidal protein into a plant genome. The shuttle vector is similar to that used by C. L. Fink (1982) M.S. thesis, University of Wisconsin-Madison, to put the nos gene into an octopine Ti plasmid. In the present invention, the protein coding sequences for nos are removed and replaced with an insecticidal gene before insertion into the Ti plasmid. The eventual result is an octopine-type Ti plasmid carrying an insecticide gene expressible in plant cells under control of a nopaline synthase promoter.

3.1 Moving the nos gene into M13mp7 pCF44 (Fink, supra) was digested with XhoI, religated to itself, and transformed back into K802. Plasmid DNA isolated from ampicillin-resistant transformants was analyzed with restriction enzymes. A plasmid having a single XhoI site within its Ti plasmid-derived DNA sequences was designated pCF44A. The single XhoI site was the result of the deletion of a DNA fragment between the two pCF44 XhoI sites. Deletion of this XhoI fragment resulted in the complete removal of two inconvenient ClaI sites.

pCF44A was digested with HindIII and BamHI, mixed with and ligated to pBR322 which had been digested with the same two restriction enzymes and transformed into K802. Ampicillin resistant transformants were selected and screened by restriction enzyme analysis of plasmid DNA and a colony was identified which contained a nos gene-containing plasmid, labeled pNS5.

pNS5 was digested with BclI and BamHI and was mixed with and ligated, a double-stranded circular replicative form (RF) of the single-stranded DNA vector M13mp7 which had been linearized with BamHI. After transformation of the mixture into JM103 and selection of white plaques, two colonies were identified by restriction mapping after RF isolation, designated M13-1 and M13-3, contained the sense and antisense strands, respectively, when in single-stranded form.

3.2 Placement of an NcoI site behind the nos promoter

An oligonucleotide primer having the sequence 5'AGTCTCATACTCACTCTCAATCCAAATAATCTGCCATGGAT3' was synthesized as described in Example 10.1. This oligonucleotide was changed at the underlined base from the naturally occurring sequence at the 5'-end of the nos structural gene. The change resulted in the introduction of an NcoI site, 5' . . . C*CATGG . . . 3', at the ATG translational start of the nos gene. The oligonucleotide was hybridized to circular single-stranded M13-3 DNA isolated from virions which had been sedimented out of culture medium. The oligonucleotide:M13-3 hybrid was incubated with DNA ligase and the Klenow fragment of *E. coli* DNA polymerase I, covalently closed circular DNA (cccDNA) was enriched, and the mixture was transformed into JM103. The virions produced by transformants were isolated and used to infect cells at a low multiplicity of infection. RF DNA was isolated from a number of these infected colonies and characterized by restriction mapping. Clones derived from the mutant oligonucleotide-primed strand were identified by the presence of a single NcoI site, which allowed them to be linearized by that enzyme. The mutated clones were further characterized to localize the NcoI site by digestion with ClaI, BamHI (to identify linearized molecules), and ClaI together with NcoI. The mutated M13-3 vector was labeled M13-3A/B18a.

3.3 Moving the insecticide gene into M13mp8 p123/58-10 DNA (Example 1.1) was digested with EcoRI and mixed with and ligated to EcoRI-linearized M13mp8 RF DNA. After transformation of the mixture into JM103 and selection of white plaques, two colonies having the insecticide gene-carrying fragment inserted in opposite orientations, were identified by restriction mapping. They were labeled MBT14 and MBT3 and respectively had the sense and antisense strands when in single stranded form.

3.4 Placement of an NcoI site at the insecticide gene translation start

An oligonucleotide primer having the sequence 5'GAGGTAACCCATGGATAACAAT3' is synthesized as described in Example 10.1. This oligonucleotide is changed at the two underlined bases from the naturally occurring sequence at the 5'-end of the insecticide structural gene. The change results in the introduction of an NcoI site, 5' . . . C*CATGG . . . 3' at the ATG translational start of the insecticide gene. The oligonucleotide is hybridized to circular single-stranded MBT3 DNA isolated from virions which had been sedimented out of culture medium. The oligonucleotide:MBT3 hybrid is incubated with DNA ligase and the Klenow fragment of *E. coli* DNA polymerase II, cccDNA is enriched, and the mixture is transformed into JM103. The virions produced by the transformants are isolated and used to infect cells at a low multiplicity of infection. RF DNA is isolated from a number of these infected colonies and characterized by restriction mapping. Clones derived from the mutant oligonucleotide-primed strand are identified by the presence of a single NcoI site which allows them to be linearized by that enzyme. The mutated clone is further characterized by restriction enzyme analysis and the presence of the mutant sequence is confirmed by sequencing. The plasmid having the desired sequence is labeled MBT3(Nco).

3.5 Assembly of a plant expressible insecticide gene in a shuttle vector

NcoI- and HindIII-digested MBT3(Nco) RF DNA is mixed with and ligated to a linker, synthesized as described in Example 11.1, having the following structure:

```
HindIII-end              BamHI
  5'AGCTGACTAACTAG3'
      3'CTGATTGATCCTAG5'
```

This linker encodes stop codons (underlined) in all three reading phases, and is ended by a functional BamHI site and a HindIII compatible sticky-end incapable of reconstructing a HindIII site. The insecticide gene-bearing DNA fragment is then trimmed by digestion with NcoI and BamHI and is isolated by agarose gel electrophoresis.

pKS111-N (Fink, supra) is a plasmid having a nos gene inserted in Tn5 DNA (from pKS-4) which has a functional kan gene, which is itself inserted in the T-DNA of pKS111. pKS111-N is linearized with SstII and digested to completion with BamHI. M13-3A/B18a is digested with NcoI and SstII and the SstII/NcoI promoter fragment is isolated by agarose gel electrophoresis. The SstII/NcoI promoter and NcoI/BamHI gene fragments are mixed with and ligated to the pKS111-N SstII/BamHI reaction products. The ligation mixture is then transformed into *E. coli* K802. Plasmids isolated from transformants resistant to kanamycin and tetracycline are subjected to restriction enzyme analysis and colonies harboring plasmids identical to pKS111-N except for replacement of a 5'-portion of the nos gene with an insecticide structural gene are identified. Such a plasmid is designated pKS111-NpBt.

3.6 Insertion into TIP plasmids, plant infection and regeneration

E. coli K802(pKS111-NpBt) is mated with A. tumefaciens as described in Example 9. The Agrobacterium strains chosen harbor TIP plasmids, based on pTi15955, containing mutations, such as those described in the Background, which facilitate regeneration. Homologous recombinants are selected as described in Example 9 and characterized by restriction mapping. The efficacy of the construction is quickly tested by infection of sunflower stems. The resulting galls are assayed by ELISA and Western blots as described in Example 7 and by bioassay as described in Example 8. As described in Example 6, the Agrobacterium strains are used to infect tobacco cells which are then regenerated. The resulting plants are used as breeding stock to be crossed with various commercial varieties for which insect resistance properties are desired. Regenerated plants and fields of their insecticidal protein-containing decendants are resistant to infestation by larve of insects such as tobacco hornworm by virtue of the toxic effect such larve experience when eating tissue from such plants.

EXAMPLE 4

This example teaches another method of inserting an expressible gene for the *B. thuringiensis* insecticidal protein into a plant genome. The strategy is similar to that described in Example 3 but differs in that a plant promoter is used instead of a T-DNA promoter. The plant gene providing the promoter is phaseolin, which has been shown to be active in species other than its source, the bean *Phaseolus vulgaris* L.

4.1 Moving the phaseolin gene into M13mp7

BamHI linkers, having the sequence 5'GGATCC3', are annealed to form double-stranded structures, and blunt-end ligated to form concatamers. These concatamers are partially digested with BamHI to expose 5'GATC . . . 3' sticky-ends, which are compatible with sticky-ends generated by the enzymes BamHI, BclI, BglII, MboI, Sau3AI, and XhoII (5'GATC . . . 3') A Charon 24A phage clone of phaseolin, 177.4 (S. M. Sun et al. (1981) Nature 289:37–41, J. L. Slightom et al. (1983) Proc. Natl. Acad. Sci. U.S.A. 80:1897–1901, also designated AG-PVPh177.4) is digested with BglII and BamHI, mixed with and ligated to the concatenated linkers, and completely digested with BamHI to trim the linkers and expose the BamHI sticky-ends, a 3.8 kbp fragment containing the phaseolin gene and 5'- and 3'-flanking sequences is isolated by agarose gel electrophoresis followed by elution. This fragment has BamHI sites at either end as the BamHI/BglII linkage site is not susceptible to the action of either enzyme. The 3.8 kbp BglII/BamHI fragment can also be obtained from p8.8, a pBR322 based subclone of 177.4.

The 3.8 kbp fragment is mixed with and ligated to BamHI-linearized M13mp7 RF. After transformation of the mixture into JM103 and selection of white plaques, two colonies are selected after characterization by restriction and hybridization analysis of RFs and phage DNA. The viral forms of M13-3.8A and M13-3.8S are respectively found to be carrying antisense and sense strands of the phaseolin gene.

4.2 Placement of an NcoI site behind the phaseolin promoter

The Phaseolus DNA of M13-3.8A has an NcoI site about 450 bp upstream from the phaseolin transcriptional start. The presence of this site will be inconvenient when on wishes to cleave the plasmid at the NcoI to be introduced at the phaseolin translational start Isolated M13-3.8A RF DNA is linearized with NcoI and the 5'-protruding ends are filled in by the action of the Klenow fragment of *E. coli* DNA polymerase I. After blunt-end ligation and transformation into JM103, RF DNAs are isolated and characterized by restriction mapping. A colony is chosen which harbors a vector, labeled M13-3.8Ac, which is lacking the NcoI site of the Phaseolus DNA but is otherwise unchanged from M13-3.8A.

An oligonucleotide primer having the sequence 5'ATACTACTCTACC̲ATGG̲TGAGAGCAAGGG3' is synthesized as described in Example 10.1. This oligonucleotide is changed at the underlined bases from the naturally occurring sequence at the 5'-end of the phaseolin gene. The oligonucleotide is hybridized to circular single-stranded M13-3.8Ac DNA isolated from virions which had been sedimented out of culture medium. The oligonucleotide:M13-3.8Ac hybrid is incubated with DNA ligase and the Klenow fragment of *E. coli* DNA polymerase I, cccDNA is enriched, and the mixture is transformed into JM103. The virions produced by transformants are isolated and used to infect cells at a low multiplicity of infection. RF DNA is isolated from a number of these infected colonies and characterized by restriction mapping. Clones derived from the mutant oligonucleotide-primed strand are identified by the presence of a novel NcoI site positioned at the 5'-end of the coding sequence. The mutated clones are further characterized to localize the NcoI site by digestion with ClaI and ClaI together with NcoI. The mutated M13-3.8Ac vector is labeled M13-3.8Aa.

4.3 Placement of a HindIII site at the 3'-end of the phaseolin gene

To conveniently introduce the insecticide gene into the phaseolin gene, two additional changes must be made to that phaseolin gene. The first change involves addition of HindIII site (5' . . . A*AGCTT . . . 3') 5' to the polyadenylation site and near the 3'-end of the phaseolin gene. The other important change involves placing translational stop codons (e.g. TAA, TAG, or TGA, underlined below) in all three reading frames. When the oligonucleotide 5'AGGGTGCATTTGAAGCTTGAATAAGTAAGAACTAAAATGC3' (a) is compared with the 3'-end of the phaseolin gene coding sequence (b), it can be seen to have the desired properties as follows:

```
                       HindIII
a)  5' AGGGTGCATTTGA*AGCTTGAATAAGTAAGAACTAAAATGC3'
b)...AGGGTGCATTTGT GTACTGAATAAGTATGAACTAAAATGC...
mismatches:         ↑  ↑↑↑↑                ↑
```

Note also that this 38-mer has only 6 mismatches, thus insuring good hybridization properties during priming.

The oligonucleotide 5'AGGGTGCATTTGAAGCT-TGAATAAGTAAGAACTAAAATGC3', synthesized as described in Example 10.1, is hybridized to single-strand circular M13-3.8Aa DNA purified from virions isolated by centrifugation of culture medium. The oligonucleotide:M13-3.8Aa hybrid is incubated with DNA ligase and the Klenow fragment of *E. coli* DNA polymerase I, cccDNA is enriched, and the mixture is transformed into JM103. The virions produced by the transformants are isolated and used to infect cells at a low multiplicity of infection. RF DNA is isolated from a number of the infected colonies and characterized by restriction enzyme analysis. Clones derived from the mutant oligonucleotide-primed strand are identified by the presence of a HindIII site mapping at the 3'-end of the phaseolin gene, and the presence of mutant sequences at both ends of the structural gene is confirmed by sequencing. A vector containing the desired sequences is labeled M13-3.8Ab.

4.4 Inserting the insecticide gene

MBT3(Nco) RF DNA is digested with NcoI and HindIII and is mixed with and ligated to NcoI- and HindIII-digested M13-3.8Ab DNA. The mixture is transformed into K802 and plasmid DNA from kanamycin and/or tetracycline resistant transformants is isolated and characterized by restriction enzyme analysis. A plasmid having the insecticide structural gene inserted between the phaseolin promoter and polyadenylation site is labeled M13-PpBt, and a colony harboring it is chosen.

4.5 Moving the modified phaseolin gene into a shuttle vector pKS111-K (Fink, supra) has the Tn5 kan gene from pKS-4 inserted between the HindIII sites of pKS111 T-DNA. M13-PpBt/RF DNA is digested with BamHI and mixed with and ligated to BamHI-linearized pKS111-K (Fink, supra). Plasmids from K802 transformants resistant to kanamycin and/or tetracycline are isolated and characterized by restriction mapping. A colony is selected which harbors a plasmid, labeled pKS111-PpBt, which contains the phaseolin promoter/insecticide structural gene/polyadenylation site combination which, together with a kan gene, is surrounded by octopine T-DNA.

4.6 Insertion into TIP plasmids, plant infection and regeneration

*E. coli* K802(pKS111-PpBt) is mated with *A. tumefaciens* as described in Example 9. The Agrobacterium strains chosen harbor TIP plasmids, based on pti15955, containing mutations, such as those described in the Background, which facilitate regeneration. Homologous recombinants are selected as described in Example 9 and characterized by restriction mapping. The efficacy of the construction is quickly tested by infection of sunflower stems. The resulting galls are assayed by ELISA and Western blots as described in Example 7 and by bioassay as described in Example 8. As described in Example 6, the Agrobacterium strains are used to infect tobacco cells which are then regenerated. The resulting plants are used as breeding stock to be crossed with various commercial varieties for which insect resistance properties are desired. Fields of regenerated plants and their insecticidal protein-containing descendants are resistant to infestation by larve of insects such as tobacco hornworm by virtue of the toxic effect such larve experience when eating tissue from such plants.

Example 5

Regeneration in this Example involves carrot tumors incited by Ri-based TIP plasmids and is effected essentially as described by M.-D. Chilton et al. (1982) Nature 295:432–434.

5.1 Infection with hairy root

Carrot disks are inoculated with about $10^9$ bacteria in 0.1 ml of water. One to 1.5 cm segments of the ends of the roots obtained are cut off, placed on solid (1–1.5% agar) Monier medium lacking hormones (D. A. Tepfer & J. C. Tempe (1981) Cr. hebd. Seanc. Acad. Sci., Paris 295:153–156), and grown at 25 C. to 27 C. in the dark. Cultures uncontaminated by bacteria are transferred every 2 to 3 weeks and are subcultured in Monier medium lacking hormones and agar. Transformed roots can be recognized by their aberrant morphology and selected.

5.2 Regeneration of roots to plants

The cultured root tissue described in Example 5.1 is placed on solidified (0.8% agar) Monier medium supplemented with 0.36 μM 2,4-D and 0.72 μM kinetin. After 4 weeks, the resulting callus tissue is placed in liquid Monier medium lacking hormones. During incubation at 22 to 25 C. on a shaker (150 r.p.m.) for one month, the callus disassociates into a suspension culture from which embryos differentiate, which, when placed in Petri dishes containing Monier medium lacking hormone, develop into plantlets. These plantlets are grown in culture, and after "hardening" by exposure to atmospheres of progressively decreasing humidity, are transferred to soil in either a greenhouse or field plot.

5.3 Use of non-hairy root vectors

Ti-based vectors which do not have functional tmr genes are used instead of the Ri-based vectors as described by T. C. Hall et al., U.S. applications, Ser. Nos. 485,613 and 485,614. Construction of suitable mutants can be done by those skilled in the art, and is reviewed in the Background.

Example 6

Regeneration in this Example involves tobacco tumors incited by a Ti-based TIP plasmid and is effected essentially as described by K. A. Barton et al. (1983) Cell 32:1033–1043.

6.1 Infection with crown gall

Tobacco tissue is transformed using an approach utilizing inverted stem segments first described by A. C. Braun (1956) Canc. Res. 16:53–56. Stems are surface sterilized with a solution that was 7% commercial Chlorox and 80% ethanol, rinsed with sterile distilled water, cut into 1 cm segments, placed basal end up in Petri dishes containing agar-solidified MS medium (T. Murashige & F. Skoog (1962) Physiol. Plant. 15:473–497) lacking hormones. Inoculation is effected by puncturing the cut basal surface of the stem with a syringe needle and injecting bacteria. Stems are cultured at 25 C. with 16 hours of light per day. The calli which develop are removed from the upper surface of the stem segments, are placed on solidified MS medium containing 0.2 mg/ml carbenicillin and lacking hormones, are transferred to fresh MS-carbenicillin medium three times at intervals of about a month, and are tested to ascertain whether the cultures had been ridden of bacteria. The axemic tissues are maintained on solidified MS media lacking supplements under the culture conditions (25 C.; 16 hr.:8 hr. light:dark) described above.

6.2 Culture of transformed tissue

Clones are obtained from the transformed axenic tissues as described by A. Binns & F. Meins (1979) Planta 145:365–369. Calli are converted into suspensions of cells by culturing in liquid MS having 0.02 mg/l naphtalene acetic acid (NAA) at 25 C. for 2 or 3 days while being shaken at 135 r.p.m., and filtering in turn through 543 and 213 μm stainless steel meshes. The passed filtrate is concentrated, plated in 5 ml of MS medium containing 0.5% melted agar, 2.0 mg/l NAA, 0.3 mg/l kinetin and 0.4 g/l Difco yeast extract at a density of about $8\times10^3$ cells/ml. Colonies reaching a diameter of about 1 mm are picked by scalpel point, placed onto and grown on solidified MS medium having 2.0 mg/l NAA, 0.3 mg/l kinetin and about 10 μg/ml S-(2-aminoethyl)-L-cysteine (AEC). (A range of concentrations of AEC, between about 2 μg/ml and about 30 μg/ml, is tried as the exact concentration effective for selection will depend on the variety of tobacco used and the growth conditions to which the source plant and tissues derived from it are subjected.) AEC has been shown to be an agent capable of selecting tissue containing octopine synthase (G. A. Dahl & J. Tempé (1983) Theor. Appl. Genet., in press). Alternatively, the filtrate is plated at low density (several hundred cells per ml) on a filter paper overlaying a feeder layer of tobacco cells growing on the solidified MS/NAA/kinetin/yeast extract medium. When 1 mm colonies have formed the entire filter paper is transferred to a petri dish containing the solidified MS/NAA/kinetin/AEC medium. The resulting calli which do not show the effects of AEC toxicity are selected, split into pieces, and tested for other transformed phenotypes such as production of octopine and hormone independent growth.

6.3 Regeneration of plants

Transformed clones are placed onto solidified MS medium having 0.3 mg/l kinetin, and cultured as described in Example 6.1. The shoots which form are rooted by putting them on a solid (1.0% agar) medium containing 1/10 strength MS medium salts, 0.4 mg/l thiamine, lacking sucrose and hormones, and having a pH of 7.0. Rooted plantlets are grown in culture, hardened as described in Example 5.2, and are transferred to soil in either a greenhouse or field plot. Plants are screened for retention of the transformed phenotype methods, well known to those skilled in the art, such as Southern, Northern and dot blots with appropriate probes, octopine assays, immunological (see Example 7) or biological (Example 8) assays for presence of crystal protein.

6.4 Vectors used

Constructions described by T. C. Hall et al., U.S. application Ser. Nos. 485,613 and 485,614 are suitable Ti-based vectors lacking functional tmr genes. The method described in Example 6.1 for infection of inverted stem segments is often useful for the establishment of TIP-transformed plant cell lines.

Example 7

Anti-insecticidal protein antibody was produced by methods well known to those skilled in the art of immunology. "Western" blots, to detect antigens after SDS-polyacrylamide gel electrophoresis, were done essentially as described by R. P. Legocki & D. P.S. Verma (1981) Analyt. Biochem 111:385–392.

Micro-ELISA (enzyme-linked immuno-sorbant assay) assays are done using Immulon-2 type plates having 96 wells by the following steps:

7.1 Binding antibody to plates

On day 1, the wells are coated with 1:1000 dilution of antibody (rabbit anti-insecticidal protein IgG) in coating buffer. 200 μl/well is incubated at 37 C. for 2–4 hours. The plates are covered with Saran Wrap during this incubation. Afterwards the plates are rinsed three times with phosphate buffered saline-Tween (PBS-Tween) allowing a 5 minute waiting period between each rinse step. Then 1% borine serum albumin (BSA) is added to rinse and, after addition to the well, left to sit for 20 minutes before discarding. Rinsing is repeated five times more with PBS-Tween.

7.2 Tissue homogenization

The tissue is sliced up into small pieces and then homogenized with a polytron using 1 gm of tissue/ml phosphate buffered saline-Tween-2% polyvinyl pyrrolidone-40 (PBS-Tween-2% PVP-40). All samples are kept on ice before and after grinding and standard curves were obtained. One standard curve is done in tissue homogenates and one standard curve is also done in buffer to check the recovery of insecticidal protein from homogenized tissue or cells. Following centrifugation of the homogenized samples, 100 μl of each sample is placed in a well and left overnight at 4 C. To avoid errors, duplicates of each sample are done. The plates are sealed during incubation.

7.3 Binding enzyme

After the overnight incubation, the antigen is discarded and the wells are washed five times with PBS-Tween allowing 5 minutes between each rinse.

A conjugate (rabbit anti-insecticidal protein IgG alkaline phosphatase-linked) is the diluted 1:3000 in PBS-Tween-2% PVP containing 0.2% BSA and 150 is added to each well; followed by incubation for 3–6 hours at 37 C. After the incubation, the conjugate is discarded and the wells are rinsed five times with PBS-Tween, allowing five minutes between each rinse as before.

7.4 Assay

Immediately before running the assay, a 5 mg tablet of p-nitrophenyl phosphate (obtained from Sigma and stored frozen in the dark) is added per 10 ml substrate and vortexed until the tablet is dissolved. 200 μl of the room temperature solution is quickly added to each well. The reaction is measured at various times, e.g. t=0, 10, 20, 40, 60, 90 and 120 minutes, using a Dynatech Micro-ELISA reader. When p-nitrophenyl phosphate, which is colorless, is hydrolysed by alkaline phosphatase to inorganic phosphate and p-nitrophenol, the latter compound gives the solution a yellow color, which can be spectrophotometrically read at 410 nm.

Example 8

Insects were obtained from commercial sources and kept essentially as described by R. A. Bell & F. G. Joachim (1976) Ann. Entomol. Soc. Amer. 69:365–373, or R. T. Yamamoto (1969) J. Econ. Entomol. 62:1427–1431. Bioassays for insecticidal protein were done by feeding extracts to larve of Manduca sexta essentially as described by J. H. Schesser et al. (1977) Appl. Environ. Microbiol. 33:878–880.

Example 9

Triparental matings were generally accomplished as described below; other variations known to those skilled in the art are also acceptable. E. coli K802(pRK290-based shuttle vector) was mated with E. coli (pRK2013) and a TIP plasmid harboring A. tumefaciens strain resistant to streptomycin. The pRK2013 transferred to the shuttle vector carrying strain and mobilized the shuttle vector for transfer to the Agrobacterium. Growth on a medium containing both streptomycin and the drug to which the shuttle vector is resistant, often either kanamycin or chloramphenicol, resulted in the selection of Agrobacterium cells containing shuttle vector sequences. A mating of these cells with E. coli (pPH1J1) resulted in the transfer of pPH1J1 to the Agrobacterium cells. pPH1J1 and pRK290-based shuttle vectors cannot coexist for long in the same cell. Growth on gentamycin, to which pPH1J1 carries a resistance gene, resulted in selection of cells having lost the pRK290 sequences. The only cells resistant to streptomycin, gentamycin, and kanamycin are those which have Ti plasmids that have undergone double-homologous recombination with the shuttle vector and now carry the desired construction. pRK290 and pRK2013 were disclosed by G. Ditta et al. (1980) Proc. Natl. Acad. Sci. U.S.A. 77:7347–7357, and pPH1J1 by P. R. Hirsh (1978) Thesis, Univ. E. Anglia.

Example 10

This Example describes techniques for the synthesis and use of synthetic oligonucleotides. Other useful references can be found in the list of works cited in the section introductory to these Examples.

10.1 Oligonucleotide synthesis

The techniques for chemical synthesis of DNA fragments used in these Examples utilize a number of techniques well known to those skilled in the art of DNA synthesis. The modification of nucleosides is described by H. Schallor et al. (1963) J. Amer. Chem. Soc. 85:3820, and H. Buchi & H. G. Khorana (1965) J. Amer. Chem Soc. 87:2990. The preparation of deoxynucleoside phosphoramidites is described by S. L. Beaucage & M. H. Caruthers (1981) Tetrahedron Lett. 22:1859. Preparation of solid phase resin is described by S. P. Adams et al. (1983) J. Amer. Chem. Soc. Hybridization procedures useful during the formation of double-stranded synthetic linkers are described by J. J. Rossi et al. (1982) J. Biol. Chem. 257:11070.

10.2 Use for oligonucleotides

Use of synthetic oligonucleotides to reconstruct a deleted segment of a gene has been exemplified by Hall et al., U.S. application Ser. No. 485,614. Use of synthetic oligonucleotides to link otherwise incompatible restriction site stickeyends has been exemplified by Hall et al., U.S. application Ser. No. 485,614 and is well known to those skilled in the art of recombinant DNA manipulations.

10.3 Oligonucleotide-Directed Mutagenesis

General methods of directed mutagenesis have been reviewed recently by D. Shortle et al. (1981) Ann. Rev. Genet. 15:265–294. Of special utility in manipulation of genes is oligonucleotide-directed site-specific mutagenesis, reviewed recently by M. J. Zoller & M. Smith (1983) Meth. Enzymol. 100:468–500 and M. Smith & S. Gillam (1981) in *Genetic Engineering; Principals and Methods*, Vol. 3, eds.: J. K. Setlow & A. Hollaender, and M. Smith (1982) Trends in Biochem. 7:440–442. This technique permits the change of one or more base pairs in a DNA sequence or the introduction of small insertions or deletions. Receipt examples of use of oligonucleotide-directed mutagenesis include M. J. Zoller a M. Smith (1983) supra, M. J. Zoller & M. Smith (1982) Nucleic Acids Res. 10:6487–6500, G. Dalbadie-McFarland et al. (1982) Proc. Natl. Aced. Sci. U.S.A. 79:6409–6413, G. F. M. Simons et al. (1982) Nucleic Acids Res. 10:821–832, and C. A. Hutchison III et al. (1978) J. Biol. Chem. 253:6551–6560. Useful M13-based vectors (e.g. mWB2344) have been reported by W. M. Barnes et al. (1983) Meth. Enzymol. 101:98–122, and W. M. Barnes & M. Bevan (1983) Nucleic Acids Res. 11:349–368.

The sequence to be modified usually is moved into a single-stranded bacteriophage vector, here one derived from M13, by standard techniques well known to those in the art. The vector DNA is generally in the double-stranded replicative form (RF), as the single-stranded viral form cannot ordinarily be "cut and spliced" by restriction enzymes and ligases. After in vitro ligation of the fragment into the RF, transformation into a suitable host, and production single-stranded DNA (ssDNA) as part of the life cycle of the vector. ssDNA is isolated from phage particles and hybridized to an oligonucleotide having sufficient length and sequence homology to hybridize to the vector in the appropriate location. The oligonucleotide should have the sequence desired as an end product and otherwise differ in no way from the sequence to be changed. Once a hybrid is formed comprising a ssDNA circle base paired to the oligonucleotide carrying the mutant sequence, the oligonucleotide primes synthesis of a complementary strand of DNA by the Klenow fragment of E. coli DNA polymerase I, a polymerase lacking a 5'-to-3' exonuclease activity. The vector is optionally incubated with DNA ligase and the polymerase and ligase reactions may be done simultaneously. Preferentially covalently closed-circular double-stranded DNA (cccDNA) molecules can be selected before transformation by techniques which include alkaline sucrose gradient centrifugation, extraction with phenol under alkaline conditions, and incubation with S1 nuclease. The vector can now be transformed into an appropriate bacterial host cell. Virus particles from this initial infection are isolated and used to form plaques by infecting a lawn of bacteria. In cases where one is changing a restriction site, one may readily screen RFs by restriction enzyme analysis. One may also screen by hybridization under carefully selected conditions using synthetic mutant oligonucleotide primer as a probe, or by DNA sequencing. When a clone containing the desired change has been isolated, one may manipulate the now mutant DNA as desired using techniques well known to those skilled in the art.

TABLE 1

Insects susceptible to *B. thuringiensis* insecticidal protein

COLEOPTERA

*Popillia japonica* (Japanese beetle)
*Sitophilus granarius* (granary weavil)
DIPTERA

*Aedes aegypti* (yellow-fever mosquito)
*A. atlanticus*
*A. cantans*
*A. capsius*
*A. cinereus*
*A. communis*
*A. detritus*
*A. dorsalis*
*A. dupreei*
*A. melanimon*
*A. nigromaculis* (pasture mosquito)
*A. punctor*
*A. sierrensis* (western treehole mosquito)
*A. sollicitans* (brown salt marsh mosquito)
Aedes sp.
*A. taeniorhynchus* (black salt marsh mosquito)
*A. tarsalis*
*A. tormenter*
*A. triseriatus*
*A. vexans* (inland floodwater mosquito)
*Anopheles crucians*
*A. freeborni*
*A. quadrimaculatus* (common malaria mosquito)
*A. sergentii*
*A. stephensi*
Anopheles sp.
*Chironomus plumosus* (Chironomus: midges, biting)
Chironomus sp.
*C. tummi*
*Culex erraticus*
*C. inornata*
*C. nigripalus*
*C. peus*
*C. pipiens* (northern house mosquito)
*C. quinquefasciatus* (*C. pipiens fatigans*) (southern house mosquito)
*C. restuans*
Culex sp.
*C. tritaeniorhynchus*
*C. tarsalis* (western encephalitis mosquito)
*C. territans*
*C. univittatus*
*Culiseta incidens* (Culiseta: mosquitos)
*C. inornata*
Diamessa sp.
Dixa sp. (Dixa: midges)
Eusimulium (Simulium) *latipes* (Eusimulium: gnats)
*Goeldichironomus holoprasinus*
*Haematobia irritans* (horn fly)
*Hippelates collusor*
*Odagmia ornata*
*Pales pavida*
Polpomyia sp. (Polpomyia: midges, biting)
Polypedilum sp. (Polypedilum: midges)
*Psorophora ciliata*
*P. columiae* (confinnis) (Florida Glades mosquito, dark rice field mosquito)
*P. ferox*
*Simulium alcocki* (Simulium: black flies)

TABLE 1-continued

Insects susceptible to *B. thuringiensis* insecticidal protein

*S. argus*
*S. cervicornutum*
*S. damnosum*
*S. jenningsi*
*S. piperi*
*S. tescorum*
*S. tuberosum*
*S. unicornutum*
*S. venustum*
*S. verecundum*
*S. vittatum*
*Uranotaenia inguiculata*
*U. lowii*
*Wyeomyia mitchellii* (Wyeomyia: mosquitos)
*W. vanduzeei*
HYMENOPTERA

*Athalia rosae* (as colibri)
Nematus (Pteronidea) *ribesii* (imported currantworm)
*Neodiprion banksianae* (jack-pine sawfly)
*Priophorus tristis*
*Pristiphora erichsonii* (larch sawfly)
LEPIDOPTERA

*Achaea janata*
*Achroia grisella* (lesser wax moth)
*Achyra rantalis*
*Acleris variana* (black-headed budworm)
Acrobasis sp.
*Acrolepia alliella*
Acrolepiopsis (Acrolepia) *assectella*
*Adoxophyes orana* (apple leaf roller)
Aegeria (Sanninoidea) *exitiosa* (peach tree borer)
*Aglais urticae*
Agriopsis (Erannis) *aurantiaria* (Erannis: loopers)
A. (E.) *leucophaearia*
*A. marginaria*
*Agrotis ipsilon* (as ypsilon) (black cutworm)
*A. segetum*
*Alabama argillacea* (cotton leafworm)
*Alsophila aescularia*
*A. pometaria (fall cankerworm)*
*Amorbia essigana*
Anadevidia (Plusia) *peponis*
*Anisota senatoria* (orange-striped oakworm)
*Anomis flava*
A. (Cosmophila) *sabulifera*
*Antheraea pernyi*
*Anticarsia gemmatalis* (velvetbean caterpillar)
Apocheima (Biston) *hispidaria*
*A. pilosaria (pedaria)*
*Aporia crataegi* (black-veined whitemoth)
*Archips argyrospilus* (fruit-tree leaf roller)
*A. cerasivoranus* (ugly-nest caterpillar)
*A. crataegana*
*A. podana*
A. (Cacoecia) *rosana*
*A. xylosteana*
*Arctia caja*
*Argyrotaenia mariana* (gray-banded leaf roller)
*A. velutinana (red-banded leaf roller)*
Ascia (Pieris) *monuste orseis*
*Ascotis selenaria*
*Atteva aurea* (alianthus webworm)
*Autographa californica* (alfalfa looper)
A. (Plusia) *gamma*
*A. nigrisigna*
*Autoplusia egena* (bean leaf skeletonizer)
*Azochis gripusalis*
*Bissetia steniella*
*Bombyx mori* (silkworm)
*Brachionycha sphinx*
*Bucculatrix thurberiella* (cotton leaf perforator)
*Bupolus piniarius* (Bupolus: looper)
*Cacoecimorpha pronubana*
*Cactoblastis cactorum*

TABLE 1-continued

Insects susceptible to *B. thuringiensis* insecticidal protein

Caloptilia (Gracillaria) invariabilis
C. (G) syringella (lilac leaf miner)
C. (G.) theivora
*Canephora asiatica*
*Carposina niponensis*
Ceramidia sp.
*Cerapteryx graminis*
*Chilo auricilius*
C. sacchariphagus indicus
C. suppressalis (rice stem borer)
*Choristoneura fumiferana* (spruce budworm)
C. murinana (fir-shoot roller)
Chrysodeixis (Plusia) chalcites
*Clepsis spectrana*
*Cnaphalocrocis medinalis*
Coleotechnites (Recurvaria) milleri (lodgepole needle miner)
C. nanella
Colias eurytheme (alfalfa caterpillar)
C. lesbia
*Colotois pennaria*
*Crambus bonifatellus* (fawn-colored lawn moth, sod webworm)
C. sperryellus
Crambus spp.
*Cryptoblabes gnidiella*
*Cydia funebrana*
C. (Grapholitha) molesta (oriental fruit moth)
C. (Laspeyresta) pomonella (codling moth)
*Datana integerrima* (walnut caterpillar)
*D. ministra* (yellow-necked caterpillar)
*Dendrolimus pini*
*D. sibiricus*
*Depressaria marcella* (a webworm)
*Desmia funeralis* (grape leaf folder)
*Diachrysia (Plusia) orichalcea* (a semilooper)
*Diacrisia virginica* (yellow woollybear)
*Diaphania (Margaronia) indica*
*D. nitidalis* (pickleworm)
*Diaphora mendica*
*Diatraea grandiosella* (southwestern corn borer)
*D. saccharalis* (sugarcane borer)
*Dichomeris marginella* (juniper webworm)
*Drymonia ruficornis* (as chaonia)
Drymonia sp.
*Dryocampa rubicunda*
*Earias insulana*
*Ectropis (Boarmia) crepuscularia*
*Ennomos subsignarius* (elm spanworm)
*Ephestia (Cadra) cautella* (almond moth)
*E. elutella* (tobacco moth)
E. (Anagasta) kuehniella (Mediterranean flour moth)
*Epinotia tsugana* (a skeletonizer)
*Epiphyas postvittana*
*Erannis defoliaria* (mottled umber moth)
*E. tiliaria* (linden looper)
*Erinnysis ello*
*Eriogaster henkei*
*E. lanestris*
*Estigmene acrea* (salt marsh caterpillar)
*Eublemma amabilis*
*Euphydryas chalcedona*
*Eupoecilia ambiguella*
*Euproctis chrysorrhoea (Nygmi phaeorrhoea)* (brown tail moth)
*E. fraterna*
*E. pseudoconspersa*
*Eupterote fabia*
Eutromula (Simaethis) pariana
*Euxoa messoria* (dark-sided cutworm)
*Galleria mellonella* (greater wax moth)
*Gastropacha quercifolia*
*Halisdota argentata*
*H. caryae* (hickory tussock moth)
*Harrisina brillians* (western grape skeletonizer)
*Hedya nubiferana* (fruit tree tortrix moth)
Heliothis (Helicoverpa) armigera (Heliothis = Chloridea) (gram pod borer)
H. (H.) assulta
*Heliothis peltigera*

TABLE 1-continued

Insects susceptible to *B. thuringiensis* insecticidal protein

H. virescens (tobacco budworm)
*H. viriplaca*
H. zea (cotton bollworm, corn earworm, soybean podworm, tomato fruitworm, sorghum headworm, etc.)
Hellula undalis (cabbage webworm)
*Herpetogramma phaeopteralis*
*Heterocampa guttivitta* (saddled prominent)
H. manteo (variable oak leaf caterpillar)
*Holcocera pulverea*
Homoeosoma electellum (sunflower moth)
*Homona magnanima*
*Hyloicus pinastri*
*Hypeuryntis coricopa*
*Hyphantria cunea* (fall webworm)
*Hypogymna morio*
Itame (Thamnonoma) wauaria (a spanworm)
Junonia coenia (buckeye caterpillars)
*Kakivoria flavofasciata*
Keiferia (Gnorimoschema) lycopersicella (tomato pinworm)
Lacanobia (Polia) oleracea
*Lamdina athasaria pellucidaria*
*L. fiscellaria fiscellaria* (hemlock looper)
*L. fisellaria lugubrosa*
*L. fiscellaria somniaria*
*Lampides boeticus*
Leucoma (Stilpnotia) salicis (satin moth)
*L. wiltshirei*
Lobesia (= Polychrosis) botrana
*Loxostege commixtalis* (alfalfa webworm)
*L. sticticalis* (beet webworm)
Lymantria (Porthetria) dispar (gypsy moth) (Lymantria: tussock moths)
*L. monacha* (nun-moth caterpillar)
*Malacosoma americana* (eastern tent caterpillar)
*M. disstria* (forest tent caterpillar)
*M. fragilis* (= fragile) (Great Basin tent caterpillar)
*M. neustria* (tent caterpillar, lackey moth)
*M. neustria var. testacea*
*M. pluviale* (western tent caterpillar)
*Mamerstra brassicae* (cabbage moth)
Manduca (Inotoparce) quinquemaculata (tomato hornworm)
M. (I.) sexta (tobacco hornworm)
*Maruca testulalis*
*Melanolophia imitata*
*Mesographe forficalis*
*Mocis repanda* (Mocis: semilooper)
*Molippa sabina*
*Monema flavescens*
Mythimna (Pseudaletia) unipuncta (armyworm)
*Nephantis serinopa*
Noctua (Triphaena) pronuba
*Nomophila noctuella* (lucerne moth)
*Nymphalis antiOpa* (mourning-cloak butterfly)
*Oiketicus moyanoi*
*Ommatopteryx texana*
*Operophtera brumata* (winter moth)
Opsophanes sp.
*O. fagata*
Orgyia (Hemerocampa) antiqua
*O. leucostigma* (white-marked tussock moth)
O. (H.) pseudotsugata (Douglas-fir tussock moth)
*O. thyellina*
*Orthosia gothica*
Ostrinia (Pyrausta) nubilalis (European corn borer)
*Paleacrita vernata* (spring cankerworm)
*Pammene juliana*
*Pandemis dumetana*
*P. pyrusana*
*Panolis flammea*
*Papilio cresphontes* (orange dog)
*P. philenor*
Paralipsa (Aphemia) gularis
*Paralobesia viteana*
*Paramyelois transitella*
*Parnara guttata*
Pectinophora gossypiella (pink bollworm)
*Pericallia ricini*

TABLE 1-continued

Insects susceptible to *B. thuringiensis* insecticidal protein

*Peridroma saucia* (variegated cutworm)
*Phalera bucephala*
*Phlogophora meticulosa*
*Phryganidia californica* (California oakworm)
*Phthorimaea* (= *Gnorimoschema*) *operculella* (potato tuberworms)
*Phyllonorycter* (*Lithocolletis*) *blancardella*
*Pieris brassicae* (large white butterfly)
*P. canidia sordida*
*P. rapae* (imported cabbageworm, small white butterfly)
*Plathypena scabra* (green cloverworm)
*Platynota* sp.
*P. stultana*
*Platyptilia carduidactyla* (artichoke plume moth)
*Plodia interpunctella* (Indian-meal moth)
*Plutella xylostella* as *maculipennis* (diamondback moth)
*Prays citri* (citrus flower moth)
*P. oleae* (olive moth)
*Pseudoplusia includens* (soybean looper)
*Pygaera anastomosis*
*Rachiplusia ou*
*Rhyacionia buoliana* (European pine shoot moth)
*Sabulodes caberata*
*Samia cynthia*
*Saturnia pavonia*
*Schizura concinna* (red-humped caterpillar)
*Schoenobius bipunctifer*
*Selenephera lunigera*
*Sesamia inferens*
*Sibine apicalis*
*Sitotroga cerealella* (Angoumois grain moth)
*Sparganothis pilleriana*
*Spilonota* (*Tmetocera*) *ocellana* (eye-spotted budmoth)
*Spilosoma lubricipeda* (as *menthastri*)
*S. virginica*
*Spilosoma* sp.
*Spodoptera* (*Prodenia*) *eridania* (southern armyworm)
*S. exigua* (beet armyworm, lucerne caterpillar)
*S. frugiperda*
*S. littoralis*
*S. litura*
*S. mauritia*
*S. (P.) ornithogalli* (yellow-striped armyworm)
*S. (P.) praefica*
*Syllepte derogata*
*S. silicalis*
*Symmerista canicosta*
*Thaumetopoea pityocampa* (pine processionary caterpillar)
*T. processionea*
*T. wauaria* (currant webworm)
*T. wilkinsoni*
*Thymelicus lineola* (European skipper)
*Thyridopteryx ephemeraeformis* (bagworm)
*Tineola bisselliella* (webbing clothes moth)
*Tortrix viridana* (oalt tortricid)
*Trichoplusia ni* (cabbage looper)
*Udea profundalis* (celery leaf tier)
*U. rubigalis*
*Vanessa cardui* (painted-lady)
*V. io*
*Xanthopastis timais*
*Xestia* (*Amathes*, *Agrotis*) *c-nigrum* (spotted cutworm)
*Yponomeuta cognatella* (= *Y. evonymi*) (*Yponomeuta* = *Hyponomeuta*)
*Y. evonymella*
*Y. mahalebella*
*Y. malinella* (small ermine moth)
*Y. padella* (small ermine moth)
*Y. rorrella*
*Zeiraphera diniana*
MALLOPHAGA

*Bovicola bovis* (cattle biting louse)
*B. crassipes*
*B. limbata*
*B. ovis*
*Lipeurus caponis* (wing louse)

TABLE 1-continued

Insects susceptible to *B. thuringiensis* insecticidal protein

*Menacnathus stramineus*
*Menopon gallinae* (shaft louse)
TRICHOPTERA

*Hydropsyche pellucida*
*Potamophylax rotundipennis*

TABLE 2

Plants recommended for protection by *B. thuringinensis* insecticidal protein

| | | |
|---|---|---|
| alfalfa | escarole | potatoes |
| almonds | field corn | radishes |
| apples | filberts | rangeland |
| artichokes | flowers | raspberries |
| avocados | forage crops | safflower |
| bananas | forest trees | shade trees |
| beans | fruit trees | shingiku |
| beets | garlic | small grains |
| blackberries | grapes | soybeans |
| blueberries | hay | spinach |
| broccoli | kale | squash |
| brussels sprouts | kiwi | stonefruits |
| cabbage | kohlrabi | stored corn |
| caneberries | lentils | stored grains |
| carrots | lettuce | stored oilseeds |
| cauliflower | melons | stored peanuts |
| celery | mint | stored soybeans |
| chard | mustard greens | stored tobacco |
| cherries | nectarines | strawberries |
| chinese cabbage | onions | sugarbeets |
| chrysanthemums | oranges | sugar maple |
| citrus | ornamental trees | sunflower |
| collards | parsley | sweet corn |
| cos lettuce | pasture | sweet potatoes |
| cotton | peaches | tobacco |
| cranberries | peanuts | tomatoes |
| crop seed | pears | turf |
| cucumbers | peas | turnip greens |
| currants | pecans | walnuts |
| dewberries | peppers | watermelons |
| eggplant | pome fruit | |
| endive | pomegranite | |

TABLE 3

Varieties of *B. thuringiensis*

*aleati*
*aizawai*
*canadensis*
*dakota*
*darmstadiensis*
*dendrolimus*
*entomocidus*
*finitimus*
*fowleri*
*galleriae*
*indiana*
*israelensis*
*kenyae*
*kurstaki*
*kyushuensis*
*morrisoni*
*ostriniae*
*pakistani*
*sotto*
*thompsoni*
*thuringiensis*
*tolworthi*
*toumanoffi*
*wuhanensis*

TABLE 4

Index of plasmids and strains

| Strain or Plasmid | Constructed or Used in Example | See Figure | Made From (& Comments) |
|---|---|---|---|
| A. tumefaciens | 6 | | (ubiquitous) |
| A. rhizogenes | 5 | | (also see background) |
| B. thuringiensis var. kurstaki HD-73 | 1.1 | 1 | |
| ColE1 | 2.5 | | |
| E. coli GM33 | 2.3 | | |
| E. coli HB101 | 1.1 | | |
| E. coli JH103 | 2.1 | | |
| E. coli K802 | 2.2 | | |
| MBT3 | 3.3 | | M13mp8, p123/58-10 |
| MBT3(Nco) | 3.4 | | MBT3 |
| MBT14 | 3.3 | | M13mp8, p123/58-10 |
| mWB2344 | 2.1 | | |
| M13-Bt-A | 2.1 | | mWB2344, p123/58-10 |
| M13-Bt-A(Bam) | 2.1 | | M13-Bt-A |
| M13-Bt-S | 2.1 | | mWB2344, p123/58-10 |
| M13mp7 | 3.1 | | |
| M13mp8 | 3.3 | | |
| M13-PpBt | 4.4 | | MBT3(Nco), M13-3.8Ab |
| M13-1 | 3.1 | | M13mp7, pNS5 |
| M13-3 | 3.1 | | M13mp7, pNS5 |
| M13-3A/B18a | 3.2 | | M13-3 |
| M13-3.8A | 4.1 | | M13mp7, 177.4 |
| M13-3.8Aa | 4.2 | | M13-3.8Ac |
| M13-3.8Ab | 4.3 | | M13-3.SAa |
| M13-3.8Ac | 4.2 | | M13-3.8A |
| M13-3.8S | 4.1 | | M13mp7, 177.4 |
| pBR322 | 1.1 | | |
| PCF44 | 3.1 | | pBR322, pTiC58 |
| pCF44A | 3.1 | | pCF44 |
| pKS-proI | 2.2 | 3 | pKS111 |
| pKS-proI(Bam) | 2.2 | 2.2 | pKS-proI |
| pKS-4 | 2.5 | 2 | pBR322, pRZ102 |
| pKS111 | 2.2 | 2, 3 | pRK290, pTi15955 |
| pKS111-K | 4.5 | | pKS4(pRZ102), pKS111 |
| pKS111-N | 3.5 | | pCF44, pKS111-K |
| PKS111-NpBt | 3.5 | | MBT3(Nco), M13-3A/B18a, pKS111-N |
| PKS111-PpBt | 4.5 | | M13-PpBt, pKS111-K |
| pNS5 | 3.1 | | pBr322, pCF44A |
| pPh1J1 | 9 | | |
| pRK290 | 2.2, 9 | | |
| pRK2013 | 9 | | |
| pRZ102 | 2.5 | | ColE1, Tn5 |
| pTiA66 | 2.4 | | |
| pTi15955 | 2.4 | 2 | |
| p8.8 | 4.1 | | pBR322, 177.4 |
| p11-83a | 2.3 | 3 | pKS-proI(Bam), pKS-4 |
| p11-83b | 2.3 | 3 | p11-83a, M13-Bt-A (Bam) |
| p123/58-3 | 1.1 | 1 | B. thuringiensis var. kurstaki HD-73, pBR322 |
| p123/58-10 | 1.1 | 1 | B. thuringiensis var. kurstaki HD-73, pBR322 |
| p403 | 2.2 | 2 | pBR322, pTi15955 |
| "1.6" | 2.2 | 2 | (= transcript 24, see also Detailed Description) |
| 177.4 | 4.1 | | Charon 24A, P. vulgaris cv. Tendergreen |

TABLE 5

| Deposited Strains | |
|---|---|
| NRRL B-4488 | Bacillus thuringiensis var. kurstaki HD-73 |
| NRRL B-15394 | Escherichig coil C600 (pKS-4) |
| NRRL B-11371 | Escherichia coli HB101 |
| NRRL B-12014 | Escherichia coli RR1 (pBR322) |
| ATCC 37017 | pBR322 |
| ATCC 15955 | Agrobacterium tumefaciens (pTi15955) |
| NRRL B-15393 | Escherichia coli HB101 (p8.8) |
| NRRL B-15612 | Escherichia coli HB101 (p123/58-10) |

We claim:

1. A truncated *Bacillus thuringiensis* delta-endotoxin having the amino acid sequence shown in FIG. 1.

* * * * *

UNITED STATES PATENT AND TRADEMARK OFFICE
CERTIFICATE OF CORRECTION

Page 1 of 4

PATENT NO. : 5,578,702

DATED : November 26, 1996

INVENTOR(S) : Michael J. Adang

It is certified that error appears in the above-identifie d patent and that said Letters Patent is hereby corrected as shown below:

Column 2, line 5: "Bactlli" should read --Bacilli--

Column 6, line 21: "cam" sould read --can--;

line 27: "Mátron" should read --Márton--.

Column 7, line 41: "In7" should read --Tn7--

Column 11, lines 66&67: "seeds he bean" should read --seeds of the bean--

Column 12, line 29: "Belt sville Syrup" should read --Beltsville Symp.--

Column 13, line 17: "Sinai" should read --SmaI--;

line 35: "within tissue" should read --within its tissue--.

line 59: "*subtilis*" should read --*subtillis*--

Column 14, line 15: "co,ton" should read --cotton--;

line 39: "frown" should read --from--;

line 60: "Insecticidal" should read --insecticidal--.

line 66: "FIG. 1" should read --Figure 1A-C (per amendment 5/19/94)

Column 16, line 37: "tins" should read --tms--

UNITED STATES PATENT AND TRADEMARK OFFICE
CERTIFICATE OF CORRECTION

PATENT NO. : 5,578,702

DATED : November 26, 1996

INVENTOR(S) : Michael J. Adang

It is certified that error appears in the above-identifie d patent and that said Letters Patent is hereby corrected as shown below:

Column 17, line 4: "thin" should read --within--;

line 18: "tern" should read --term--;

line 39: "for" should read --or--;

line 51: "Hellothis," should read --Heliothis,--;

line 61: "phosphatrsses," should read -- phosphatres --.

Column 18, line 65: "to "downstream"" should read --to lie "downstream"--.

Column 19, line 18: "teemed" should read --termed--.

Column 20, line 20: "replacing" should read --replicating--;

line 32: "chat" should read --that--.

Column 21, line 10: "tile" should read --the--;

line 62: "System" should read --Systems--;

line 64: "system" should read --systems--.

Column 23, line 35: "BglI" should read --BclI--;

line 36: "BglI" should read --BclI--.

UNITED STATES PATENT AND TRADEMARK OFFICE
CERTIFICATE OF CORRECTION

Page 3 of 4

PATENT NO.    :   5,578,702

DATED         :   November 26, 1996

INVENTOR(S)   :   Michael J. Adang

It is certified that error appears in the above-identifie d patent and that said Letters Patent is hereby corrected as shown below:

Column 24, line 33: "transformation" should read --transformants--

Column 25, line 15: "obtained" should read --observed--

Column 26, line 14: "she" should read --the--;

line 34: "arid" should read --and--;

line 44: "geese-bearing" should read --gene-bearing--;

line 59: "can brought" should read --can be brought--.

Column 27, line 40: "... 1'" should read --... 3'--.

Column 28, line 3: "Sinai site" should read --SmaI site--;

line 34: "pti 15955" should read --pTi 15955--;

line 40: "pti 15955" should read --pTi 15955--;

line 41: "pti 15955" should read --pTi 15955--.

Column 32, line 7: "carrying antisense" should read --carrying the antisense--

Column 33, line 58: "pti 15955" should read --pTi 15955--

UNITED STATES PATENT AND TRADEMARK OFFICE
CERTIFICATE OF CORRECTION

PATENT NO. : 5,578,702

DATED : November 26, 1996

INVENTOR(S) : Michael J. Adang

It is certified that error appears in the above-identifie d patent and that said Letters Patent is hereby corrected as shown below:

Column 38, line 29: "Receipt" should read --Recent--

Column 39, line 5: "using synthetic" should read --using the synthetic--

Column 39, line 34: "*A. tormenter*" should read --*A. tormentor*--

Column 42, line 47: "antiOpa" should read --antiopa--

Column 43, line 49: "oalt" should read --oak--

Column 44, line 47: "aleati" should read --alesti--

Column 46, Table 5, line 34: "*Escherinchig coil*" should read --*Escherinchia coli*--

Signed and Sealed this

Twenty-eighth Day of October, 1997

Attest:

BRUCE LEHMAN

*Attesting Officer*  *Commissioner of Patents and Trademarks*